US008173396B2

(12) United States Patent
Gardner et al.

(10) Patent No.: US 8,173,396 B2
(45) Date of Patent: May 8, 2012

(54) METHODS FOR REDUCING GLUCONOYLATION OF PROTEINS

(75) Inventors: Alan R. Gardner, King of Prussia, PA (US); Thomas D. Sweitzer, King of Prussia, PA (US); Alexander H. Taylor, King of Prussia, PA (US); Pramathesh S. Patel, King of Prussia, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 1571 days.

(21) Appl. No.: 10/547,860

(22) PCT Filed: Mar. 4, 2004

(86) PCT No.: PCT/US2004/006507
§ 371 (c)(1),
(2), (4) Date: Sep. 2, 2005

(87) PCT Pub. No.: WO2004/078936
PCT Pub. Date: Sep. 16, 2004

(65) Prior Publication Data
US 2009/0233333 A1 Sep. 17, 2009

Related U.S. Application Data

(60) Provisional application No. 60/451,686, filed on Mar. 4, 2003.

(51) Int. Cl.
C12P 21/04 (2006.01)
C12N 9/00 (2006.01)
C12N 9/18 (2006.01)
C12N 1/20 (2006.01)
C12N 15/00 (2006.01)
C07H 21/04 (2006.01)

(52) U.S. Cl. .................. 435/69.52; 435/183; 435/252.3; 435/320.1; 536/23.2

(58) Field of Classification Search .................. None
See application file for complete search history.

(56) References Cited

U.S. PATENT DOCUMENTS

| | | | |
|---|---|---|---|
| 5,426,034 A | 6/1995 | Moellering et al. | |
| 5,643,758 A | 7/1997 | Guan et al. | |
| 5,733,762 A | 3/1998 | Midoux et al. | |
| 5,948,681 A | 9/1999 | Scanlin et al. | |

OTHER PUBLICATIONS

Hager et al. J Bacteriol. Jul. 2000;182(14):3934-41.*
Kupor, et al., "6-Phosphogluconolactonase mutants of *Escherichia coli* and a maltose blue gene," *J. Bacteriol.* (Dec. 1969) 100(3):1296-1301.
Kupor, et al., "Glucose Metabolism in 6-Phosphogluconolactonase Mutants of *Escherichia coli*," *The Journal of Biological Chemistry* (1972) 247(6): 1904-1910.
Nanba, et al., "Production of thermotolerant N-Carbamyl-D-Amino Acid amidohydrolase by recombinant *Escherichia coli*," *J. Biosci. Bioeng.* (1999) 87(2):149-154.
Madurawe, et al., "A recombinant lipoprotein antigen against lyme disease expressed in *E. coli*: Fermentor operating strategies for improved yield," *Biotechnol. Prog.* (2000) 16:571-576.
Zimenkov, et al., "*Eschericia coli* ORF *yhbE* is *pgl* gene encoding 6-phosphogluconolactonase (EC 3.1.1.31) that has no homology with known 6-PGLs from other organisms," *FEMS Microbiology Letters* (2005) 244:275-280.
Kim, et al., "Post-translational modifications of the N-terminal his tag interferes with the crystallization of the wild-type and mutant SH3 domains from chicken src tyrosine kinase," *Acta. Cryst.* (2001) D57: 759-762.
Gracie, et al., "Interleukin-18," *J. Leukocyte Biology* (Feb. 2003)73:213-224.
Studier, et al., "Use of Bacteriophage T7 RNA Polymerase to Direct Selective High-level Expression of Cloned Genes," *J. Mol. Biol.* (1986) 189:113-130.
Katsura, Isao, "Structure and Inherent Properties of the Bacteriophage Lambda Head Shell," *J. Mol. Biol.* (1989) 205:397-405.
Geoghegan, et al., "Spontaneous α-N-6-Phosphogluconoylation of a 'His Tag' in *Escherichia coli*: The Cause of Extra Mass of 258 or 178 Da in Fusion Proteins," *Anal Biochem.* (1999) 267(1): 169-84.
Hager, et al., "The *Pseudomonas aeruginosa devB/SOL* Homolog, *pgl*, Is a Member of the *hex* Regulon and Encodes 6-Phosphoguconolactonase," *J. of Bacteriology* (2000) 182(14): 3934-3941.
Konz, et al., "Effects of Oxygen on Recombinant Protein Expression," *Biotechnol. Prog.* (1998) 14:393-409.
Lindsay, et al., "The effect of δ-gluconolactone, an oxidized analogue of glucose, on the nonenzymatic glycation of human and and rat haemoglobin," *Clinica Chimica Acta* (1997) 263:239-247.
Rakitzis, et al., "Reactivity of 6-phosphogluconolactone with hydroxylamine: The possible involvement of glucose-6-phosphate dehydrogenase in endogenous glycation reactions," *Chemico-Biological Interactions* (1998) 113:205-216.
Vassileva-Atanassova, et al., "N-terminal methionine in recombinant proteins expressed in two different *Escherichia coli* strains," *Journal of Biotechnology* (1999) 69:63-67.
Yamashita, et al., "Purification of Bovine S100Al2 from Recombinant *Escherichia coli*," *Protein Expression and Purification* (1999) 16:47-52.
Yan, et al., "Identification of a Gluconic Acid Derivative Attached to the N-Termus of Histidine-Tagged proteins Expressed in Bacteria," *Biochemical and Biophysical Research Communicationt* (1999)1304:793-800.
Yan, et al., "Mass Spectrometric Determination of a Novel Modification of the N-Terminus of Histidine-Tagged Proteins Expressed in Bacteria," *Biochemical and Biophysical Research Communications* (1999) 0770:271-282.
Miclet, et al. "NMR Spectroscopic Analysis of the First Two Steps of the Pentose-Phosphate Pathway Elucidates the Role of 6-Phosphogluconolactonase," *Journal of Biological Chemistry* (Sep. 2001) 276(37): 34840-34846.
Paillard, Florence, "Commentary—Glycotargeting: A Receptor-Mediated Delivery Using Sugar Ligands," *Human Gene Therapy* (1999) 10(3): 395-406.

(Continued)

Primary Examiner — Christian Fronda
(74) Attorney, Agent, or Firm — Jonathan M. Dermott; William T. Han

(57) ABSTRACT

The present invention relates to methods of preventing glyconoylation of polypeptides produced in micororganisms.

10 Claims, 14 Drawing Sheets

OTHER PUBLICATIONS

Kollen, et al., "Gluconoylated and Glycosylated Polylysines as Vectors for Gene Transfer into Cystic Fibrosis Airway Epithelial Cells," *Human Gene Therapy*(Aug. 1996) 7:1577-1586.

Erbacher, et al., "The reduction of the positive charges of polylysine by partial gluconolyation increases the transfection efficiency of polylysine/DNA complexes," *Biochim. Biophys. Acta.* (1997) 1324(1): 27-36.

Erbacher, et al., "Specific Gene Transfer Based on Biotinylated and Gluconoylated Polylysine/Plasmid Complexes" *Drug Delivery* (1997), 4(3): 173-179.

Iacobellas, Michael, "The formation of gluconyl peptides during the heating of amino acids and glucose in alkaline buffer solutions," *Archives of Biochemistry and Biophysics* (1955) 59(1): 199-206.

Serveau, et al., "New substrate of papain, based on the conserved sequence of natural inhibitors of the cystatin family," *Biochimie* (1994) 76(2): 153-158.

Harnois-Pantoni, et al., "Hydrosoluble fluorogenic substrates for plasmin," *Anal. Biochem.* (1991) 193(2): 248-255.

Fajac, et al., "Sugar-Mediated Uptake of Glycosylated Polylysines and Gene Transfer into Normal and Cystic Fibrosis Airway Epithelial Cells," *Human Gene Therapy* (Feb. 1999) 10:395-406.

Thomason, et al., "Identification of the *Escherichia coli* K-12 ybhE Gene As pgl, Encoding 6-phosphogluconolacatonase," *Journal of Bacteriology* 186(24):8248-8253 (Dec. 2004).

Klemm, et al., "The gntP gene of *Escherichia coli* Involved in Gluconate Uptake," *Journal of Bacteriology* 178(1):61-67 (Jan. 1996).

Khanna, et al., "Involvement of the pgl gene of *Escherichia coli* in Transposition," *Plasmid* 17(1):82 (1987).

Scopes, "6 Phosphogluconolactonase From Zymomonas-mobilis an Enzyme of High Catalytic Efficiency," *FEBS Letters*, 193(2):185-188 (1985).

Clarke, et al., "Glucose-6-phosphate dehydrogenase-6-phosphogluconolactonase. A Novel Bifunctional Enzyme in Malaria Parasites," *European Journal of Biochemistry* 268(7):2013-2019 (Apr. 2001).

Clarke, et al, "A Unique Insertion in *Plasmodium berghei* glucose-6-phosphate dehydrogenase-6-phosphogluconolactonase: Evolutionary and Functional Studies," *Molecular and Biochemical Parasitology*, 127(1):1-8 (Mar. 2003).

* cited by examiner

SEQ ID NO:9
DNA
pECO-1pglc12-13

```
   1  GAATTCCGGA TGAGCATTCA TCAGGCGGGC AAGAATGTGA ATAAAGGCCG GATAAAACTT
  61  GTGCTTATTT TTCTTTACGG TCTTTAAAAA GGCCGTAATA TCCAGCTGAA CGGTCTGGTT
 121  ATAGGTACAT TGAGCAACTG ACTGAAATGC CTCAAAATGT TCTTTACGAT GCCATTGGGA
 181  TATATCAACG GTGGTATATC CAGTGATTTT TTTCTCCATT TTAGCTTCCT TAGCTCCTGA
 241  AAATCTCGAT AACTCAAAAA ATACGCCCGG TAGTGATCTT ATTTCATTAT GGTGAAAGTT
 301  GGAACCTCTT ACGTGCCGAT CAACGTCTCA TTTTCGCCAA AAGTTGGCCC AGGGCTTCCC
 361  GGTATCAACA GGGACACCAG GATTTATTTA TTCTGCGAAG TGATCTTCCG TCACAGGTAT
 421  TTATTCGGCG CAAAGTGCGT CGGGTGATGC TGCCAACTTA CTGATTTAGT GTATGATGGT
 481  GTTTTTGAGG TGCTCCAGTG GCTTCTGTTT CTATCAGCTG TCCCTCCTGT TCAGCTACTG
 541  ACGGGGTGGT GCGTAACGGC AAAAGCACCG CCGGACATCA GCGCTAGCGG AGTGTATACT
 601  GGCTTACTAT GTTGGCACTG ATGAGGGTGT CAGTGAAGTG CTTCATGTGG CAGGAGAAAA
 661  AAGGCTGCAC CGGTGCGTCA GCAGAATATG TGATACAGGA TATATTCCGC TTCCTCGCTC
 721  ACTGACTCGC TACGCTCGGT CGTTCGACTG CGGCGAGCGG AAATGGCTTA CGAACGGGGC
 781  GGAGATTTCC TGGAAGATGC CAGGAAGATA CTTAACAGGG AAGTGAGAGG GCCGCGGCAA
 841  AGCCGTTTTT CCATAGGCTC CGCCCCCTG ACAAGCATCA CGAAATCTGA CGCTCAAATC
 901  AGTGGTGGCG AAACCCGACA GGACTATAAA GATACCAGGC GTTTCCCCCT GGCGGCTCCC
 961  TCGTGCGCTC TCCTGTTCCT GCCTTTCGGT TTACCGGTGT CATTCCGCTG TTATGGCCGC
1021  GTTTGTCTCA TTCCACGCCT GACACTCAGT TCCGGGTAGG CAGTTCGCTC CAAGCTGGAC
1081  TGTATGCACG AACCCCCCGT TCAGTCCGAC CGCTGCGCCT TATCCGGTAA CTATCGTCTT
1141  GAGTCCAACC CGGAAAGACA TGCAAAAGCA CCACTGGCAG CAGCCACTGG TAATTGATTT
1201  AGAGGAGTTA GTCTTGAAGT CATGCGCCGG TTAAGGCTAA ACTGAAAGGA CAAGTTTTGG
1261  TGACTGCGCT CCTCCAAGCC AGTTACCTCG GTTCAAAGAG TTGGTAGCTC AGAGAACCTT
1321  CGAAAAACCG CCCTGCAAGG CGGTTTTTTC GTTTTCAGAG CAAGAGATTA CGCGCAGACC
1381  AAAACGATCT CAAGAAGATC ATCTTATTAA TCAGATAAAA TATTTCTAGA TTTCAGTGCA
1441  ATTTATCTCT TCAAATGTAG CACCTGAAGT CAGCCCCATA CGATATAAGT TGTAATTCTC
1501  ATGTTTGACA GCTTATCATC GATAAGCTTT AATGCGGTAG TTTATCACAG TTAAATTGCT
1561  AACGCAGTCA GGCACCGTGT CATATGGATC CCGGGTACCG TCGAGCTCGA GCTCGGTGGC
1621  CCTGGTGGCC CGCGATGGGA GGAGTTGGTA TGGCGATTTC TGAGTTGAAG CTGCCGGCCG
1681  GCGTCGGCCT GCAGGTCTGG GGCAGCGCCG CCGAGCAGGC CCGCGGCCTG GCCGCCGAGG
1741  TCGCCGGCCG GTTGCGCTCG GCGCTGGCCG AGCAGGGCCA GGCGCTGCTG GTGGTGTCCG
1801  GTGGGCGCAG TCCGGTGGCC TTCCTCGAAG CCTTGAGCGA GGAGCCGCTG GACTGGTCGC
1861  GGATCACCGT CAGCCTGGCC GACGAGCGCT GGGTGCCGGA GTCGCATGCC GATAGCAACG
1921  CCGGCCTGGT TCGCCGCCAC CTGCTCCGTG GCGAGGCGGC GAAGGCGCGC TTCATCGGCC
1981  TCTACCAGCC GGCGGCGAGC CTGGAGGAAG CGGCCGAGCT GGCCGACCAT CACCTGCACG
2041  AGCTGCCATT GCCGATCGAC GTGCTGGTCC TCGGCATGGG CGACGACGGC CATACCGCCT
2101  CGCTGTTCCC GAACAGCCCT GGCCTGGACC TGGCGATGGA TCCCCAGGGG ACGCGCCGTT
2161  GCCTGCCGAT GTGGGCGCCG AGCGTGCCGC ACCAGCGCCT GACCCTGCCG CGCGCCGTGC
2221  TGGCGGCGGC GAAGGTGCAG CTGCTGGCGA TCCAGGGCCA GTCCAAGCTG GCCACCCTGA
2281  ACGCCGCGCT GGCGGTCGAG GACGAACGGC GGATGCCGGT TCGCGCCTTC CTCCGCGCGC
```

Figure 2A

```
2341  CGCTGACGAT CCATTGGTAC CCCTGAGTGG CGGACTCGAC TAGTCAACGC CATGAGCGGC
2401  CTCATTTCTT ATTCTGAGTT ACAACAGTCC GCACCGCTGT CCGGTAGCTC CTTCCGGTGG
2461  GCGCGGGGCA TGACTATCGT CGCCGCACTT ATGACTGTCT TCTTTATCAT GCAACTCGTA
2521  GGACAGGTGC CGGCAGCGCC AACAGTCCC CCGGCCACGG GGCCTGCCAC CATACCCACG
2581  CCGAAACAAG CGCCCTGCAC CATTATGTTC CGGATCTGCA TCGCAGGATG CTGCTGGCTA
2641  CCCTGTGGAA CACCTACATC TGTATTAACG AAGCGCTAAC CGTTTTTATC AGGCTCTGGG
2701  AGGCAGAATA AATGATCATA TCGTCAATTA TTACCTCCAC GGGGAGAGCC TGAGCAAACT
2761  GGCCTCAGGC ATTTGAGAAG CACACGGTCA CACTGCTTCC GGTAGTCAAT AAACCGGTAA
2821  ACCAGCAATA GACATAAGCG GCTATTTAAC GACCCTGCCC TGAACCGACG ACCGGGTCGA
2881  ATTTGCTTTC GAATTTCTGC CATTCATCCG CTTATTATCA CTTATTCAGG CGTAGCACCA
2941  GGCGTTTAAG GGCACCAATA ACTGCCTTAA AAAAATTACG CCCCGCCCTG CCACTCATCG
3001  CAGTACTGTT GTAATTCATT AAGCATTCTG CCGACATGGA AGCCATCACA GACGGCATGA
3061  TGAACCTGAA TCGCCAGCGG CATCAGCACC TTGTCGCCTT GCGTATAATA TTTGCCCATG
3121  GTGAAAACGG GGGCGAAGAA GTTGTCCATA TTGGCCACGT TTAAATCAAA ACTGGTGAAA
3181  CTCACCCAGG GATTGGCTGA GACGAAAAAC ATATTCTCAA TAAACCCTTT AGGGAAATAG
3241  GCCAGGTTTT CACCGTAACA CGCCACATCT TGCGAATATA TGTGTAGAAA CTGCCGGAAA
3301  TCGTCGTGGT ATTCACTCCA GAGCGATGAA AACGTTTCAG TTTGCTCATG GAAAACGGTG
3361  TAACAAGGGT GAACACTATC CCATATCACC AGCTCACCGT CTTTCATTGC CATACG
```

Figure 2B

SEQ ID NO:13
DNA
pET28ProIL18Casp5

```
   1  TGGCGAATGG GACGCGCCCT GTAGCGGCGC ATTAAGCGCG GCGGGTGTGG TGGTTACGCG
  61  CAGCGTGACC GCTACACTTG CCAGCGCCCT AGCGCCCGCT CCTTTCGCTT TCTTCCCTTC
 121  CTTTCTCGCC ACGTTCGCCG GCTTTCCCCG TCAAGCTCTA AATCGGGGGC TCCCTTTAGG
 181  GTTCCGATTT AGTGCTTTAC GGCACCTCGA CCCCAAAAAA CTTGATTAGG GTGATGGTTC
 241  ACGTAGTGGG CCATCGCCCT GATAGACGGT TTTTCGCCCT TTGACGTTGG AGTCCACGTT
 301  CTTTAATAGT GGACTCTTGT TCCAAACTGG AACAACACTC AACCCTATCT CGGTCTATTC
 361  TTTTGATTTA TAAGGGATTT TGCCGATTTC GGCCTATTGG TTAAAAAATG AGCTGATTTA
 421  ACAAAAATTT AACGCGAATT TTAACAAAAT ATTAACGTTT ACAATTTCAG GTGGCACTTT
 481  TCGGGGAAAT GTGCGCGGAA CCCCTATTTG TTTATTTTTC TAAATACATT CAAATATGTA
 541  TCCGCTCATG AATTAATTCT TAGAAAAACT CATCGAGCAT CAAATGAAAC TGCAATTTAT
 601  TCATATCAGG ATTATCAATA CCATATTTTT GAAAAAGCCG TTTCTGTAAT GAAGGAGAAA
 661  ACTCACCGAG GCAGTTCCAT AGGATGGCAA GATCCTGGTA TCGGTCTGCG ATTCCGACTC
 721  GTCCAACATC AATACAACCT ATTAATTTCC CCTCGTCAAA AATAAGGTTA TCAAGTGAGA
 781  AATCACCATG AGTGACGACT GAATCCGGTG AGAATGGCAA AAGTTTATGC ATTTCTTTCC
 841  AGACTTGTTC AACAGGCCAG CCATTACGCT CGTCATCAAA ATCACTCGCA TCAACCAAAC
 901  CGTTATTCAT TCGTGATTGC GCCTGAGCGA GACGAAATAC GCGATCGCTG TTAAAAGGAC
 961  AATTACAAAC AGGAATCGAA TGCAACCGGC GCAGGAACAC TGCCAGCGCA TCAACAATAT
1021  TTTCACCTGA ATCAGGATAT TCTTCTAATA CCTGGAATGC TGTTTTCCCG GGGATCGCAG
1081  TGGTGAGTAA CCATGCATCA TCAGGAGTAC GGATAAAATG CTTGATGGTC GGAAGAGGCA
1141  TAAATTCCGT CAGCCAGTTT AGTCTGACCA TCTCATCTGT AACATCATTG GCAACGCTAC
1201  CTTTGCCATG TTTCAGAAAC AACTCTGGCG CATCGGGCTT CCCATACAAT CGATAGATTG
1261  TCGCACCTGA TTGCCCGACA TTATCGCGAG CCCATTTATA CCCATATAAA TCAGCATCCA
1321  TGTTGGAATT TAATCGCGGC CTAGAGCAAG ACGTTTCCCG TTGAATATGG CTCATAACAC
1381  CCCTTGTATT ACTGTTTATG TAAGCAGACA GTTTTATTGT TCATGACCAA AATCCCTTAA
1441  CGTGAGTTTT CGTTCCACTG AGCGTCAGAC CCCGTAGAAA AGATCAAAGG ATCTTCTTGA
1501  GATCCTTTTT TTCTGCGCGT AATCTGCTGC TTGCAAACAA AAAAACCACC GCTACCAGCG
1561  GTGGTTTGTT TGCCGGATCA AGAGCTACCA ACTCTTTTTC CGAAGGTAAC TGGCTTCAGC
1621  AGAGCGCAGA TACCAAATAC TGTCCTTCTA GTGTAGCCGT AGTTAGGCCA CCACTTCAAG
1681  AACTCTGTAG CACCGCCTAC ATACCTCGCT CTGCTAATCC TGTTACCAGT GGCTGCTGCC
1741  AGTGGCGATA AGTCGTGTCT TACCGGGTTG GACTCAAGAC GATAGTTACC GGATAAGGCG
1801  CAGCGGTCGG GCTGAACGGG GGGTTCGTGC ACACAGCCCA GCTTGGAGCG AACGACCTAC
1861  ACCGAACTGA GATACCTACA GCGTGAGCTA TGAGAAAGCG CCACGCTTCC CGAAGGGAGA
1921  AAGGCGGACA GGTATCCGGT AAGCGGCAGG GTCGGAACAG GAGAGCGCAC GAGGGAGCTT
1981  CCAGGGGGAA ACGCCTGGTA TCTTTATAGT CCTGTCGGGT TTCGCCACCT CTGACTTGAG
2041  CGTCGATTTT TGTGATGCTC GTCAGGGGGG CGGAGCCTAT GGAAAAACGC CAGCAACGCG
2101  GCCTTTTTAC GGTTCCTGGC CTTTTGCTGG CCTTTTGCTC ACATGTTCTT TCCTGCGTTA
2161  TCCCCTGATT CTGTGGATAA CCGTATTACC GCCTTTGAGT GAGCTGATAC CGCTCGCCGC
2221  AGCCGAACGA CCGAGCGCAG CGAGTCAGTG AGCGAGGAAG CGGAAGAGCG CCTGATGCGG
2281  TATTTTCTCC TTACGCATCT GTGCGGTATT TCACACCGCA TATATGGTGC ACTCTCAGTA
```

Figure 4A

```
2341  CAATCTGCTC TGATGCCGCA TAGTTAAGCC AGTATACACT CCGCTATCGC TACGTGACTG
2401  GGTCATGGCT GCGCCCCGAC ACCCGCCAAC ACCCGCTGAC GCGCCCTGAC GGGCTTGTCT
2461  GCTCCCGGCA TCCGCTTACA GACAAGCTGT GACCGTCTCC GGGAGCTGCA TGTGTCAGAG
2521  GTTTTCACCG TCATCACCGA AACGCGCGAG GCAGCTGCGG TAAAGCTCAT CAGCGTGGTC
2581  GTGAAGCGAT TCACAGATGT CTGCCTGTTC ATCCGCGTCC AGCTCGTTGA GTTTCTCCAG
2641  AAGCGTTAAT GTCTGGCTTC TGATAAAGCG GGCCATGTTA AGGGCGGTTT TTTCCTGTTT
2701  GGTCACTGAT GCCTCCGTGT AAGGGGGATT TCTGTTCATG GGGGTAATGA TACCGATGAA
2761  ACGAGAGAGG ATGCTCACGA TACGGGTTAC TGATGATGAA CATGCCCGGT TACTGGAACG
2821  TTGTGAGGGT AAACAACTGG CGGTATGGAT GCGGCGGGAC CAGAGAAAAA TCACTCAGGG
2881  TCAATGCCAG CGCTTCGTTA ATACAGATGT AGGTGTTCCA CAGGGTAGCC AGCAGCATCC
2941  TGCGATGCAG ATCCGGAACA TAATGGTGCA GGGCGCTGAC TTCCGCGTTT CCAGACTTTA
3001  CGAAACACGG AAACCGAAGA CCATTCATGT TGTTGCTCAG GTCGCAGACG TTTTGCAGCA
3061  GCAGTCGCTT CACGTTCGCT CGCGTATCGG TGATTCATTC TGCTAACCAG TAAGGCAACC
3121  CCGCCAGCCT AGCCGGGTCC TCAACGACAG GAGCACGATC ATGCGCACCC GTGGGGCCGC
3181  CATGCCGGCG ATAATGGCCT GCTTCTCGCC GAAACGTTTG GTGGCGGGAC CAGTGACGAA
3241  GGCTTGAGCG AGGGCGTGCA AGATTCCGAA TACCGCAAGC GACAGGCCGA TCATCGTCGC
3301  GCTCCAGCGA AAGCGGTCCT CGCCGAAAAT GACCCAGAGC GCTGCCGGCA CCTGTCCTAC
3361  GAGTTGCATG ATAAAGAAGA CAGTCATAAG.TGCGGCGACG ATAGTCATGC CCCGCGCCCA
3421  CCGGAAGGAG CTGACTGGGT TGAAGGCTCT CAAGGGCATC GGTCGAGATC CCGGTGCCTA
3481  ATGAGTGAGC TAACTTACAT TAATTGCGTT GCGCTCACTG CCCGCTTTCC AGTCGGGAAA
3541  CCTGTCGTGC CAGCTGCATT AATGAATCGG CCAACGCGCG GGGAGAGGCG GTTTGCGTAT
3601  TGGGCGCCAG GGTGGTTTTT CTTTTCACCA GTGAGACGGG CAACAGCTGA TTGCCCTTCA
3661  CCGCCTGGCC CTGAGAGAGT TGCAGCAAGC GGTCCACGCT GGTTTGCCCC AGCAGGCGAA
3721  AATCCTGTTT GATGGTGGTT AACGGCGGGA TATAACATGA GCTGTCTTCG GTATCGTCGT
3781  ATCCCACTAC CGAGATATCC GCACCAACGC GCAGCCCGGA CTCGGTAATG GCGCGCATTG
3841  CGCCCAGCGC CATCTGATCG TTGGCAACCA GCATCGCAGT GGGAACGATG CCCTCATTCA
3901  GCATTTGCAT GGTTTGTTGA AAACCGGACA TGGCACTCCA GTCGCCTTCC CGTTCCGCTA
3961  TCGGCTGAAT TTGATTGCGA GTGAGATATT TATGCCAGCC AGCCAGACGC AGACGCGCCG
4021  AGACAGAACT TAATGGGCCC GCTAACAGCG CGATTTGCTG GTGACCCAAT GCGACCAGAT
4081  GCTCCACGCC CAGTCGCGTA CCGTCTTCAT GGGAGAAAAT AATACTGTTG ATGGGTGTCT
4141  GGTCAGAGAC ATCAAGAAAT AACGCCGGAA CATTAGTGCA GGCAGCTTCC ACAGCAATGG
4201  CATCCTGGTC ATCCAGCGGA TAGTTAATGA TCAGCCCACT GACGCGTTGC GCGAGAAGAT
4261  TGTGCACCGC CGCTTTACAG GCTTCGACGC CGCTTCGTTC TACCATCGAC ACCACCACGC
4321  TGGCACCCAG TTGATCGGCG CGAGATTTAA TCGCCGCGAC AATTTGCGAC GGCGCGTGCA
4381  GGGCCAGACT GGAGGTGGCA ACGCCAATCA GCAACGACTG TTTGCCCGCC AGTTGTTGTG
4441  CCACGCGGTT GGGAATGTAA TTCAGCTCCG CCATCGCCGC TTCCACTTTT TCCCGCGTTT
4501  TCGCAGAAAC GTGGCTGGCC TGGTTCACCA CGCGGGAAAC GGTCTGATAA GAGACACCGG
4561  CATACTCTGC GACATCGTAT AACGTTACTG GTTTCACATT CACCACCCTG AATTGACTCT
4621  CTTCCGGCG CTATCATGCC ATACCGCGAA AGGTTTTGCG CCATTCGATG GTGTCCGGGA
4681  TCTCGACGCT CTCCCTTATG CGACTCCTGC ATTAGGAAGC AGCCCAGTAG TAGGTTGAGG
4741  CCGTTGAGCA CCGCCGCCGC AAGGAATGGT GCATGCAAGG AGATGGCGCC CAACAGTCCC
4801  CCGGCCACGG GGCCTGCCAC CATACCCACG CCGAAACAAG CGCTCATGAG CCCGAAGTGG
```

Figure 4B

```
4861  CGAGCCCGAT CTTCCCCATC GGTGATGTCG GCGATATAGG CGCCAGCAAC CGCACCTGTG
4921  GCGCCGGTGA TGCCGGCCAC GATGCGTCCG GCGTAGAGGA TCGAGATCTC GATCCCGCGA
4981  AATTAATACG ACTCACTATA GGGGAATTGT GAGCGGATAA CAATTCCCCT CTAGACCACA
5041  CCTTAAGGAG GATATAACAT ATGGCTGCTG AACCAGTAGA AGACAATTGC ATCAACTTTG
5101  TGGCAATGAA ATTTATTGAC AATACGCTTT ACTTTATAGC TGAAGATGAT GAAAACCTGG
5161  AATCAGATTA CTTTGGCAAG CTTGAGAGCA AACTATCGGT CATTCGTAAT TTAAATGACC
5221  AGGTCCTATT TATCGACCAA GGGAATCGTC CACTATTCGA GGACATGACA GACAGTGACT
5281  GCCGAGACAA TGCGCCGCGA ACCATTTTCA TTATATCTAT GTACAAGGAT TCTCAGCCGC
5341  GCGGAATGGC CGTAACTATT TCTGTCAAAT GTGAAAAGAT ATCCACGCTG TCGTGTGAGA
5401  ACAAGATTAT TAGTTTCAAA GAGATGAATC CGCCGGATAA TATCAAGGAC ACGAAGTCTG
5461  ATATCATATT TTTCCAGCGC AGCGTGCCGG GGCACGATAA CAAGATGCAA TTTGAATCAT
5521  CCAGCTATGA AGGGTACTTT CTTGCATGCG AGAAGGAACG CGATCTCTTT AAACTTATTT
5581  TAAAGAAAGA GGACGAGCTA GGCGATCGCA GCATTATGTT CACTGTCCAA AATGAAGACT
5641  AGTGGAGGAT ATAATACCAG GAATAAATAA AATCCATGGG CCATCATCAT CATCATCATG
5701  GCATACTCAA ACTTTGTCCT CGTGAAGAAT TCCTGAGACT GTGTAAAAAA AATCATGATG
5761  AGATCTATCC AATAAAAAAG AGAGGACC GCAGACGCCT GGCTCTCATC ATATGCAATA
5821  CAAAGTTTGA TCACCTGCCT GCAAGGAATG GGGCTCACTA TGACATCGTG GGGATGAAAA
5881  GGCTGCTTCA AGGCCTGGGC TACACTGTGG TTGACGAAAA GAATCTCACA GCCAGGGATA
5941  TGGAGTCAGT GCTGAGGGCA TTTGCTGCCA GACCAGAGCA CAAGTCCTCT GACAGCACGT
6001  TCTTGGTACT CATGTCTCAT GGCATCCTAG AGGGAATCTG CGGAACTGCG CATAAAAAGA
6061  AAAAACCGGA TGTGCTGCTT TATGACACCA TCTTCCAGAT ATTCAACAAC CGCAACTGCC
6121  TCAGTCTAAA GGACAAACCC AAGGTCATCA TTGTCCAGGC CTGCAGAGGT GAAAAACATG
6181  GGGAACTCTG GGTCAGAGAC TCTCCAGCAT CCTTGGCAGT CATCTCTTCA CAGTCATCTG
6241  AGAACTGGA GGCAGATTCT GTTTGCAAGA TCCACGAGGA GAAGGACTTC ATTGCTTTCT
6301  GTTCTTCAAC ACCACATAAC GTGTCCTGGA GAGACCGCAC AAGGGGCTCC ATCTTCATTA
6361  CGGAACTCAT CACATGCTTC AGAAATATT CTTGCTGCTG CCACCTAATG GAAATATTTC
6421  GGAAGGTACA GAAATCATTT GAAGTTCCAC AGGCTAAAGC CCAGATGCCC ACCATAGAAC
6481  GAGCAACCTT GACAAGAGAT TTCTACCTCT TTCCTGGCAA TTGACTCGAG CACCACCACC
6541  ACCACCACTG AGATCCGGCT GCTAACAAAG CCCGAAAGGA AGCTGAGTTG GCTGCTGCCA
6601  CCGCTGAGCA ATAACTAGCA TAACCCCTTG GGGCCTCTAA ACGGGTCTTG AGGGGTTTTT
6661  TGCTGAAAGG AGGAACTATA TCCGGBT
```

Figure 4C

SEQ ID NO:14
DNA
pET28proIL18casp5+pg1

```
   1 TGGCGAATGG GACGCGCCCT GTAGCGGCGC ATTAAGCGCG GCGGGTGTGG TGGTTACGCG
  61 CAGCGTGACC GCTACACTTG CCAGCGCCCT AGCGCCCGCT CCTTTCGCTT TCTTCCCTTC
 121 CTTTCTCGCC ACGTTCGCCG GCTTTCCCCG TCAAGCTCTA AATCGGGGGC TCCCTTTAGG
 181 GTTCCGATTT AGTGCTTTAC GGCACCTCGA CCCCAAAAAA CTTGATTAGG GTGATGGTTC
 241 ACGTAGTGGG CCATCGCCCT GATAGACGGT TTTTCGCCCT TTGACGTTGG AGTCCACGTT
 301 CTTTAATAGT GGACTCTTGT TCCAAACTGG AACAACACTC AACCCTATCT CGGTCTATTC
 361 TTTTGATTTA TAAGGGATTT TGCCGATTTC GGCCTATTGG TTAAAAAATG AGCTGATTTA
 421 ACAAAAATTT AACGCGAATT TTAACAAAAT ATTAACGTTT ACAATTTCAG GTGGCACTTT
 481 TCGGGGAAAT GTGCGCGGAA CCCCTATTTG TTTATTTTTC TAAATACATT CAAATATGTA
 541 TCCGCTCATG AATTAATTCT TAGAAAAACT CATCGAGCAT CAAATGAAAC TGCAATTTAT
 601 TCATATCAGG ATTATCAATA CCATATTTTT GAAAAAGCCG TTTCTGTAAT GAAGGAGAAA
 661 ACTCACCGAG GCAGTTCCAT AGGATGGCAA GATCCTGGTA TCGGTCTGCG ATTCCGACTC
 721 GTCCAACATC AATACAACCT ATTAATTTCC CCTCGTCAAA AATAAGGTTA TCAAGTGAGA
 781 AATCACCATG AGTGACGACT GAATCCGGTG AGAATGGCAA AAGTTTATGC ATTTCTTTCC
 841 AGACTTGTTC AACAGGCCAG CCATTACGCT CGTCATCAAA ATCACTCGCA TCAACCAAAC
 901 CGTTATTCAT TCGTGATTGC GCCTGAGCGA GACGAAATAC GCGATCGCTG TTAAAAGGAC
 961 AATTACAAAC AGGAATCGAA TGCAACCGGC GCAGGAACAC TGCCAGCGCA TCAACAATAT
1021 TTTCACCTGA ATCAGGATAT TCTTCTAATA CCTGGAATGC TGTTTTCCCG GGGATCGCAG
1081 TGGTGAGTAA CCATGCATCA TCAGGAGTAC GGATAAAATG CTTGATGGTC GGAAGAGGCA
1141 TAAATTCCGT CAGCCAGTTT AGTCTGACCA TCTCATCTGT AACATCATTG GCAACGCTAC
1201 CTTTGCCATG TTTCAGAAAC AACTCTGGCG CATCGGGCTT CCCATACAAT CGATAGATTG
1261 TCGCACCTGA TTGCCCGACA TTATCGCGAG CCCATTTATA CCCATATAAA TCAGCATCCA
1321 TGTTGGAATT TAATCGCGGC CTAGAGCAAG ACGTTTCCCG TTGAATATGG CTCATAACAC
1381 CCCTTGTATT ACTGTTTATG TAAGCAGACA GTTTTATTGT TCATGACCAA AATCCCTTAA
1441 CGTGAGTTTT CGTTCCACTG AGCGTCAGAC CCCGTAGAAA AGATCAAAGG ATCTTCTTGA
1501 GATCCTTTTT TTCTGCGCGT AATCTGCTGC TTGCAAACAA AAAAACCACC GCTACCAGCG
1561 GTGGTTTGTT TGCCGGATCA AGAGCTACCA ACTCTTTTTC CGAAGGTAAC TGGCTTCAGC
1621 AGAGCGCAGA TACCAAATAC TGTCCTTCTA GTGTAGCCGT AGTTAGGCCA CCACTTCAAG
1681 AACTCTGTAG CACCGCCTAC ATACCTCGCT CTGCTAATCC TGTTACCAGT GGCTGCTGCC
1741 AGTGGCGATA AGTCGTGTCT TACCGGGTTG GACTCAAGAC GATAGTTACC GGATAAGGCG
1801 CAGCGGTCGG GCTGAACGGG GGGTTCGTGC ACACAGCCCA GCTTGGAGCG AACGACCTAC
1861 ACCGAACTGA GATACCTACA GCGTGAGCTA TGAGAAAGCG CCACGCTTCC CGAAGGGAGA
1921 AAGGCGGACA GGTATCCGGT AAGCGGCAGG GTCGGAACAG GAGAGCGCAC GAGGGAGCTT
1981 CCAGGGGGAA ACGCCTGGTA TCTTTATAGT CCTGTCGGGT TTCGCCACCT CTGACTTGAG
2041 CGTCGATTTT TGTGATGCTC GTCAGGGGGG CGGAGCCTAT GGAAAAACGC CAGCAACGCG
2101 GCCTTTTTAC GGTTCCTGGC CTTTTGCTGG CCTTTTGCTC ACATGTTCTT TCCTGCGTTA
2161 TCCCCTGATT CTGTGGATAA CCGTATTACC GCCTTTGAGT GAGCTGATAC CGCTCGCCGC
2221 AGCCGAACGA CCGAGCGCAG CGAGTCAGTG AGCGAGGAAG CGGAAGAGCG CCTGATGCGG
2281 TATTTTCTCC TTACGCATCT GTGCGGTATT TCACACCGCA TATATGGTGC ACTCTCAGTA
```

Figure 6A

```
2341  CAATCTGCTC TGATGCCGCA TAGTTAAGCC AGTATACACT CCGCTATCGC TACGTGACTG
2401  GGTCATGGCT GCGCCCCGAC ACCCGCCAAC ACCCGCTGAC GCGCCCTGAC GGGCTTGTCT
2461  GCTCCCGGCA TCCGCTTACA GACAAGCTGT GACCGTCTCC GGGAGCTGCA TGTGTCAGAG
2521  GTTTTCACCG TCATCACCGA AACGCGCGAG GCAGCTGCGG TAAAGCTCAT CAGCGTGGTC
2581  GTGAAGCGAT TCACAGATGT CTGCCTGTTC ATCCGCGTCC AGCTCGTTGA GTTTCTCCAG
2641  AAGCGTTAAT GTCTGGCTTC TGATAAAGCG GGCCATGTTA AGGGCGGTTT TTTCCTGTTT
2701  GGTCACTGAT GCCTCCGTGT AAGGGGGATT TCTGTTCATG GGGGTAATGA TACCGATGAA
2761  ACGAGAGAGG ATGCTCACGA TACGGGTTAC TGATGATGAA CATGCCCGGT TACTGGAACG
2821  TTGTGAGGGT AAACAACTGG CGGTATGGAT GCGGCGGGAC CAGAGAAAAA TCACTCAGGG
2881  TCAATGCCAG CGCTTCGTTA ATACAGATGT AGGTGTTCCA CAGGGTAGCC AGCAGCATCC
2941  TGCGATGCAG ATCCGGAACA TAATGGTGCA GGGCGCTGAC TTCCGCGTTT CCAGACTTTA
3001  CGAAACACGG AAACCGAAGA CCATTCATGT TGTTGCTCAG GTCGCAGACG TTTTGCAGCA
3061  GCAGTCGCTT CACGTTCGCT CGCGTATCGG TGATTCATTC TGCTAACCAG TAAGGCAACC
3121  CCGCCAGCCT AGCCGGGTCC TCAACGACAG GAGCACGATC ATGCGCACCC GTGGGGCCGC
3181  CATGCCGGCG ATAATGGCCT GCTTCTCGCC GAAACGTTTG GTGGCGGGAC CAGTGACGAA
3241  GGCTTGAGCG AGGGCGTGCA AGATTCCGAA TACCGCAAGC GACAGGCCGA TCATCGTCGC
3301  GCTCCAGCGA AAGCGGTCCT CGCCGAAAAT GACCCAGAGC GCTGCCGGCA CCTGTCCTAC
3361  GAGTTGCATG ATAAAGAAGA CAGTCATAAG TGCGGCGACG ATAGTCATGC CCCGCGCCCA
3421  CCGGAAGGAG CTGACTGGGT TGAAGGCTCT CAAGGGCATC GGTCGAGATC CCGGTGCCTA
3481  ATGAGTGAGC TAACTTACAT TAATTGCGTT GCGCTCACTG CCCGCTTTCC AGTCGGGAAA
3541  CCTGTCGTGC CAGCTGCATT AATGAATCGG CCAACGCGCG GGGAGAGGCG GTTTGCGTAT
3601  TGGGCGCCAG GGTGGTTTTT CTTTTCACCA GTGAGACGGG CAACAGCTGA TTGCCCTTCA
3661  CCGCCTGGCC CTGAGAGAGT TGCAGCAAGC GGTCCACGCT GGTTTGCCCC AGCAGGCGAA
3721  AATCCTGTTT GATGGTGGTT AACGGCGGGA TATAACATGA GCTGTCTTCG GTATCGTCGT
3781  ATCCCACTAC CGAGATATCC GCACCAACGC GCAGCCCGGA CTCGGTAATG GCGCGCATTG
3841  CGCCCAGCGC CATCTGATCG TTGGCAACCA GCATCGCAGT GGGAACGATG CCCTCATTCA
3901  GCATTTGCAT GGTTTGTTGA AAACCGGACA TGGCACTCCA GTCGCCTTCC CGTTCCGCTA
3961  TCGGCTGAAT TTGATTGCGA GTGAGATATT TATGCCAGCC AGCCAGACGC AGACGCGCCG
4021  AGACAGAACT TAATGGGCCC GCTAACAGCG CGATTTGCTG GTGACCCAAT GCGACCAGAT
4081  GCTCCACGCC CAGTCGCGTA CCGTCTTCAT GGGAGAAAAT AATACTGTTG ATGGGTGTCT
4141  GGTCAGAGAC ATCAAGAAAT AACGCCGGAA CATTAGTGCA GGCAGCTTCC ACAGCAATGG
4201  CATCCTGGTC ATCCAGCGGA TAGTTAATGA TCAGCCCACT GACGCGTTGC GCGAGAAGAT
4261  TGTGCACCGC CGCTTTACAG GCTTCGACGC CGCTTCGTTC TACCATCGAC ACCACCACGC
4321  TGGCACCCAG TTGATCGGCG CGAGATTTAA TCGCCGCGAC AATTTGCGAC GGCGCGTGCA
4381  GGGCCAGACT GGAGGTGGCA ACGCCAATCA GCAACGACTG TTTGCCCGCC AGTTGTTGTG
4441  CCACGCGGTT GGGAATGTAA TTCAGCTCCG CCATCGCCGC TTCCACTTTT TCCCGCGTTT
4501  TCGCAGAAAC GTGGCTGGCC TGGTTCACCA CGCGGGAAAC GGTCTGATAA GAGACACCGG
4561  CATACTCTGC GACATCGTAT AACGTTACTG GTTTCACATT CACCACCCTG AATTGACTCT
4621  CTTCCGGGCG CTATCATGCC ATACCGCGAA AGGTTTTGCG CCATTCGATG GTGTCCGGGA
4681  TCTCGACGCT CTCCCTTATG CGACTCCTGC ATTAGGAAGC AGCCCAGTAG TAGGTTGAGG
4741  CCGTTGAGCA CCGCCGCCGC AAGGAATGGT GCATGCAAGG AGATGGCGCC CAACAGTCCC
4801  CCGGCCACGG GGCCTGCCAC CATACCCACG CCGAAACAAG CGCTCATGAG CCCGAAGTGG
```

Figure 6B

```
4861  CGAGCCCGAT CTTCCCCATC GGTGATGTCG GCGATATAGG CGCCAGCAAC CGCACCTGTG
4921  GCGCCGGTGA TGCCGGCCAC GATGCGTCCG GCGTAGAGGA TCGAGATCTC GATCCCGCGA
4981  AATTAATACG ACTCACTATA GGGGAATTGT GAGCGGATAA CAATTCCCCT CTAGACCACA
5041  CCTTAAGGAG GATATAACAT ATGGCTGCTG AACCAGTAGA AGACAATTGC ATCAACTTTG
5101  TGGCAATGAA ATTTATTGAC AATACGCTTT ACTTTATAGC TGAAGATGAT GAAAACCTGG
5161  AATCAGATTA CTTTGGCAAG CTTGAGAGCA AACTATCGGT CATTCGTAAT TTAAATGACC
5221  AGGTCCTATT TATCGACCAA GGGAATCGTC CACTATTCGA GGACATGACA GACAGTGACT
5281  GCCGAGACAA TGCGCCGCGA ACCATTTTCA TTATATCTAT GTACAAGGAT TCTCAGCCGC
5341  GCGGAATGGC CGTAACTATT TCTGTCAAAT GTGAAAAGAT ATCCACGCTG TCGTGTGAGA
5401  ACAAGATTAT TAGTTTCAAA GAGATGAATC CGCCGGATAA TATCAAGGAC ACGAAGTCTG
5461  ATATCATATT TTTCCAGCGC AGCGTGCCGG GGCACGATAA CAAGATGCAA TTTGAATCAT
5521  CCAGCTATGA AGGGTACTTT CTTGCATGCG AGAAGGAACG CGATCTCTTT AAACTTATTT
5581  TAAAGAAAGA GGACGAGCTA GGCGATCGCA GCATTATGTT CACTGTCCAA AATGAAGACT
5641  AGTGGAGGAT ATAATACCAG GAATAAATAA AATCCATGGG CCATCATCAT CATCATCATG
5701  GCATACTCAA ACTTTGTCCT CGTGAAGAAT TCCTGAGACT GTGTAAAAAA AATCATGATG
5761  AGATCTATCC AATAAAAAAG AGAGAGGACC GCAGACGCCT GGCTCTCATC ATATGCAATA
5821  CAAAGTTTGA TCACCTGCCT GCAAGGAATG GGGCTCACTA TGACATCGTG GGGATGAAAA
5881  GGCTGCTTCA AGGCCTGGGC TACACTGTGG TTGACGAAAA GAATCTCACA GCCAGGGATA
5941  TGGAGTCAGT GCTGAGGGCA TTTGCTGCCA GACCAGAGCA CAAGTCCTCT GACAGCACGT
6001  TCTTGGTACT CATGTCTCAT GGCATCCTAG AGGGAATCTG CGGAACTGCG CATAAAAAGA
6061  AAAACCGGA TGTGCTGCTT TATGACACCA TCTTCCAGAT ATTCAACAAC CGCAACTGCC
6121  TCAGTCTAAA GGACAAACCC AAGGTCATCA TTGTCCAGGC CTGCAGAGGT GAAAAACATG
6181  GGGAACTCTG GGTCAGAGAC TCTCCAGCAT CCTTGGCAGT CATCTCTTCA CAGTCATCTG
6241  AGAACCTGGA GGCAGATTCT GTTTGCAAGA TCCACGAGGA GAAGGACTTC ATTGCTTTCT
6301  GTTCTTCAAC ACCACATAAC GTGTCCTGGA GAGACCGCAC AAGGGGCTCC ATCTTCATTA
6361  CGGAACTCAT CACATGCTTC CAGAAATATT CTTGCTGCTG CCACCTAATG GAAATATTTC
6421  GGAAGGTACA GAAATCATTT GAAGTTCCAC AGGCTAAAGC CCAGATGCCC ACCATAGAAC
6481  GAGCAACCTT GACAAGAGAT TTCTACCTCT TTCCTGGCAA TTGACTCGAG CTCGGTGGCC
6541  CTGGTGGCCC GCGATGGGAG GAGTTGGTAT GGCGATTTCT GAGTTGAAGC TGCCGGCCGG
6601  CGTCGGCCTG CAGGTCTGGG GCAGCGCCGC CGAGCAGGCC CGCGGCCTGG CCGCCGAGGT
6661  CGCCGGCCGG TTGCGCTCGG CGCTGGCCGA GCAGGGCCAG GCGCTGCTGG TGGTGTCCGG
6721  TGGGCGCAGT CCGGTGGCCT TCCTCGAAGC CTTGAGCGAG GAGCCGCTGG ACTGGTCGCG
6781  GATCACAGTC AGCCTGGCCC ACGAGCGCTG GGTGCCGGAG TCGCATGCCG ATAGCAACGC
6841  CGGCCTGGTT CGCCGCCACC TGCTCCGTGG CGAGGCGGCG AAGGCGCGCT TCATCGGCCT
6901  CTACCAGCCG GCGGCGAGCC TGGAGGAAGC GGCCGAGCTG GCCGACCATC ACCTGCACGA
6961  GCTGCCATTG CCGATCGACG TGCTGGTCCT CGGCATGGGC GACGACGGCC ATACCGCCTC
7021  GCTGTTCCCG AACAGCCCTG GCCTGGACCT GGCGATGGAT CCCCAGGGGA CGCGCCGTTG
7081  CCTGCCGATG TGGGCGCCGA GCGTGCCGCA CCAGCGCCTG ACCCTGCCGC GCGCCGTGCT
7141  GGCGGCGGCG AAGGTGCAGC TGCTGGCGAT CCAGGGCCAG TCCAAGCTGG CCACCCTGAA
7201  CGCCGCGCTG GCGGTCGAGG ACGAACGGCG GATGCCGGTT CGCGCCTTCC TCCGCGCGCC
7261  GCTGACGATC CATTGGTACC CCTGAGTGGC GGACTCGAGC ACCACCACCA CCACCACTGA
7321  GATCCGGCTG CTAACAAAGC CCGAAAGGAA GCTGAGTTGG CTGCTGCCAC CGCTGAGCAA
```

Figure 6C

```
7381  TAACTAGCAT AACCCCTTGG GGCCTCTAAA CGGGTCTTGA GGGGTTTTTT GCTGAAAGGA
7441  GGAACTATAT CCGG
```

Figure 6D

SEQ ID NO:7
DNA
*Pseudomonas aeruginosa* PGL

ATG GGA GGA GTT GGT ATG GCG ATT TCT GAG TTG AAG CTG CCG GCC GGC
GTC GGC CTG CAG GTC TGG GGC AGC GCC GCC GAG CAG GCC CGC GGC CTG
GCC GCC GAG GTC GCC GGC CGG TTG CGC TCG GCG CTG GCC GAG CAG GGC
CAG GCG CTG CTG GTG GTG TCC GGT GGG CGC AGT CCG GTG GCC TTC CTC
GAA GCC TTG AGC GAG GAG CCG CTG GAC TGG TCG CGG ATC ACC GTC AGC
CTG GCC GAC GAG CGC TGG GTG CCG GAG TCG CAT GCC GAT AGC AAC GCC
GGC CTG GTT CGC CGC CAC CTG CTC CGT GGC GAG GCG GCG AAG GCG CGC
TTC ATC GGC CTC TAC CAG CCG GCG GCG AGC CTG GAG GAA GCG GCC GAG
CTG GCC GAC CAT CAC CTG CAC GAG CTG CCA TTG CCG ATC GAC GTG CTG
GTC CTC GGC ATG GGC GAC GAC GGC CAT ACC GCC TCG CTG TTC CCG AAC
AGC CCT GGC CTG GAC CTG GCG ATG GAT CCC CAG GGG ACG CGC CGT TGC
CTG CCG ATG TGG GCG CCG AGC GTG CCG CAC CAG CGC CTG ACC CTG CCG
CGC GCC GTG CTG GCG GCG GCG AAG GTG CAG CTG CTG GCG ATC CAG GGC
CAG TCC AAG CTG GCC ACC CTG AAC GCC GCG CTG GCG GTC GAG GAC GAA
CGG CGG ATG CCG GTT CGC GCC TTC CTC CGC GCG CCG CTG ACG ATC CAT
TGG TAC CCC TGA

Figure 7

SEQ ID NO:8
amino acid
Pseudomonas aeruginosa PGL

MGGVGMAISELKLPAGVGLQVWGSAAEQARGLAAEVAGRLRSALAEQGQALLVVSGGRSPVAFLEA
LSEEPLDWSRITVSLADERWVPESHADSNAGLVRRHLLRGEAAKARFIGLYQPAASLEEAAELADH
HLHELPLPIDVLVLGMGDDGHTASLFPNSPGLDLAMDPQGTRRCLPMWAPSVPHQRLTLPRAVLAA
AKVQLLAIQGQSKLATLNAALAVEDERRMPVRAFLRAPLTIHWYP

Figure 8

SEQUENCE LISTING

```
<160> NUMBER OF SEQ ID NOS: 14

<210> SEQ ID NO 1
<211> LENGTH: 24
<212> TYPE: DNA
<213> ORGANISM: ESCHERIACHIA COLI

<400> SEQUENCE: 1
agctggccat tgctcaggtc gaag                                         24
```

```
<210> SEQ ID NO 2
<211> LENGTH: 25
<212> TYPE: DNA
<213> ORGANISM: ESCHERICHIA COLI

<400> SEQUENCE: 2
gtactgtccg gaatacacga cgatg                                           25

<210> SEQ ID NO 3
<211> LENGTH: 413
<212> TYPE: DNA
<213> ORGANISM: ESCHERICHIA COLI

<400> SEQUENCE: 3
agctggccat tgctcaggtc gaagagatgc aggcagtttc tgccgtgctt aagggcaaat     60
acaccatgac cggtgaagcc ttcgatccgg ttgaggtgga tatgggccgc agtgaggaga    120
ataacatcac gcagtccggc ggcacggagt ggagcaagcg tgacaagtcc acgtatgacc    180
cgaccgacga tatcgaagcc tacgcgctga acgccagcgg tgtggtgaat atcatcgtgt    240
tcgatccgaa aggctgggcg ctgttccgtt ccttcaaagc cgtcaaggag aagctggata    300
cccgtcgtgg ctctaattcc gagctggaga cagcggtgaa agacctgggc aaagcggtgt    360
cctataaggg gatgtatggc gatgtggcca tcgtcgtgta ttccggacag tac           413

<210> SEQ ID NO 4
<211> LENGTH: 8
<212> TYPE: PRT
<213> ORGANISM: HOMO SAPIENS

<400> SEQUENCE: 4

Asn Ile Gln Ser Val Lys Val Lys
 1               5

<210> SEQ ID NO 5
<211> LENGTH: 29
<212> TYPE: DNA
<213> ORGANISM: Pseudomonas aeruginosa

<400> SEQUENCE: 5
ggcctcgagc tcggtggccc tggtggccc                                       29

<210> SEQ ID NO 6
<211> LENGTH: 31
<212> TYPE: DNA
<213> ORGANISM: Pseudomonas aeruginosa

<400> SEQUENCE: 6
gccctcgagt ccgccactca ggggtaccaa t                                    31

<210> SEQ ID NO 7
<211> LENGTH: 732
<212> TYPE: DNA
<213> ORGANISM: Pseudomonas aeruginosa

<400> SEQUENCE: 7
atgggaggag ttggtatggc gatttctgag ttgaagctgc cggccggcgt cggcctgcag     60
gtctggggca cgccgccga gcaggcccgc ggcctggccg ccgaggtcgc cggccggttg    120
cgctcggcgc tggccgagca gggccaggcg ctgctggtgg tgtccggtgg cgcagtccg    180 gtggccttcc tcgaagcctt gagcgaggag ccgctggact ggtcgcggat caccgtcagc    240
ctggccgacg agcgctgggt gccggagtcg catgccgata gcaacgccgg cctggttcgc    300
```

```
cgccacctgc tccgtggcga ggcggcgaag gcgcgcttca tcggcctcta ccagccggcg    360
gcgagcctgg aggaagcggc cgagctggcc gaccatcacc tgcacgagct gccattgccg    420
atcgacgtgc tggtcctcgg catgggcgac gacggccata ccgcctcgct gttcccgaac    480
agccctggcc tggacctggc gatggatccc caggggacgc gccgttgcct gccgatgtgg    540
gcgccgagcg tgccgcacca gcgcctgacc ctgccgcgcg ccgtgctggc ggcggcgaag    600
gtgcagctgc tggcgatcca gggccagtcc aagctggcca ccctgaacgc gcgcgctggcg   660 gtcgaggacg aacggcggat gccggttcgc gccttcctcc gcgcgccgct gacgatccat    720
tggtacccct ga                                                        732
```

<210> SEQ ID NO 8
<211> LENGTH: 243
<212> TYPE: PRT
<213> ORGANISM: Pseudomonas aeruginosa

<400> SEQUENCE: 8

```
Met Gly Gly Val Gly Met Ala Ile Ser Glu Leu Lys Leu Pro Ala Gly
 1               5                  10                  15

Val Gly Leu Gln Val Trp Gly Ser Ala Glu Gln Ala Arg Gly Leu
            20                  25                  30

Ala Ala Glu Val Ala Gly Arg Leu Arg Ser Ala Leu Ala Glu Gln Gly
        35                  40                  45

Gln Ala Leu Leu Val Val Ser Gly Gly Arg Ser Pro Val Ala Phe Leu
    50                  55                  60

Glu Ala Leu Ser Glu Glu Pro Leu Asp Trp Ser Arg Ile Thr Val Ser
65                  70                  75                  80

Leu Ala Asp Glu Arg Trp Val Pro Glu Ser His Ala Asp Ser Asn Ala
                85                  90                  95

Gly Leu Val Arg Arg His Leu Leu Arg Gly Glu Ala Ala Lys Ala Arg
            100                 105                 110

Phe Ile Gly Leu Tyr Gln Pro Ala Ala Ser Leu Glu Glu Ala Ala Glu
        115                 120                 125

Leu Ala Asp His His Leu His Glu Leu Pro Leu Pro Ile Asp Val Leu
    130                 135                 140

Val Leu Gly Met Gly Asp Asp Gly His Thr Ala Ser Leu Phe Pro Asn
145                 150                 155                 160

Ser Pro Gly Leu Asp Leu Ala Met Asp Pro Gln Gly Thr Arg Arg Cys
                165                 170                 175

Leu Pro Met Trp Ala Pro Ser Val Pro His Gln Arg Leu Thr Leu Pro
            180                 185                 190

Arg Ala Val Leu Ala Ala Ala Lys Val Gln Leu Leu Ala Ile Gln Gly
        195                 200                 205

Gln Ser Lys Leu Ala Thr Leu Asn Ala Ala Leu Ala Val Glu Asp Glu
    210                 215                 220

Arg Arg Met Pro Val Arg Ala Phe Leu Arg Ala Pro Leu Thr Ile His
225                 230                 235                 240

Trp Tyr Pro
```

<210> SEQ ID NO 9
<211> LENGTH: 3416
<212> TYPE: DNA
<213> ORGANISM: Artificial Sequence
<220> FEATURE:
<223> OTHER INFORMATION: Comprised of PECO-1 Expression & Pseudomonas aeruginosa

<400> SEQUENCE: 9

```
gaattccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga     180
tatatcaacg gtggtatatc cagtgatttt tttctccatt ttagcttcct tagctcctga     240
aaatctcgat aactcaaaaa atacgcccgg tagtgatctt atttcattat ggtgaaagtt     300
ggaacctctt acgtgccgat caacgtctca ttttcgccaa aagttggccc agggcttccc     360
ggtatcaaca gggacaccag gatttatta ttctgcgaag tgatcttccg tcacaggtat     420
ttattcggcg caaagtgcgt cgggtgatgc tgccaactta ctgatttagt gtatgatggt     480
gttttttgagg tgctccagtg gcttctgttt ctatcagctg tccctcctgt tcagctactg     540
acggggtggt gcgtaacggc aaaagcaccg ccggacatca gcgctagcgg agtgtatact     600
ggcttactat gttggcactg atgagggtgt cagtgaagtg cttcatgtgg caggagaaaa     660
aaggctgcac cggtgcgtca gcagaatatg tgatacagga tatattccgc ttcctcgctc     720
actgactcgc tacgctcggt cgttcgactg cggcgagcgg aaatggctta cgaacggggc     780
ggagatttcc tggaagatgc caggaagata cttaacaggg aagtgagagg gccgcggcaa     840
agccgttttt ccataggctc cgcccccctg acaagcatca cgaaatctga cgctcaaatc     900
agtggtggcg aaacccgaca ggactataaa gataccaggc gtttccccct ggcggctccc     960
tcgtgcgctc tcctgttcct gcctttcggt ttaccggtgt cattccgctg ttatggccgc    1020
gtttgtctca ttccacgcct gacactcagt tccgggtagg cagttcgctc caagctggac    1080
tgtatgcacg aacccccggt tcagtccgac cgctgcgcct tatccggtaa ctatcgtctt    1140
gagtccaacc cggaaagaca tgcaaaagca ccactggcag cagccactgg taattgattt    1200
agaggagtta gtcttgaagt catgcgccgg ttaaggctaa actgaaagga caagttttgg    1260
tgactgcgct cctccaagcc agttacctcg gttcaaagag ttggtagctc agagaacctt    1320
cgaaaaaccg ccctgcaagg cggttttttc gttttcagag caagagatta cgcgcagacc    1380
aaaacgatct caagaagatc atcttattaa tcagataaaa tatttctaga tttcagtgca    1440
atttatctct tcaaatgtag cacctgaagt cagccccata cgatataagt tgtaattctc    1500
atgtttgaca gcttatcatc gataagcttt aatgcggtag tttatcacag ttaaattgct    1560
aacgcagtca ggcaccgtgt catatggatc ccgggtaccg tcgagctcga gctcggtggc    1620
cctggtggcc cgcgatggga ggagttggta tggcgatttc tgagttgaag ctgccggccg    1680
gcgtcggcct gcaggtctgg ggcagcgccg ccgagcaggc ccgcggcctg ccgccgaggg    1740
tcgccggccg gttgcgctcg gcgctggccg agcagggcca ggcgctgctg gtggtgtccg    1800
gtgggcgcag tccggtggcc ttcctcgaag ccttgagcga ggagccgctg gactggtcgc    1860
ggatcaccgt cagcctggcc gacgagcgct gggtgccgga gtcgcatgcc gatagcaacg    1920
ccggcctggt tcgccgccac ctgctccgtg gcgaggcggc gaaggcgcgc ttcatcggcc    1980
tctaccagcc ggcggcgagc ctggaggaag cggccgagct ggccgaccat cacctgcacg    2040
agctgccatt gccgatcgac gtgctggtcc tcggcatggg cgacgacggc cataccgcct    2100
cgctgttccc gaacagccct ggcctggacc tggcgatgga tccccagggg acgcgccgtt    2160
gcctgccgat gtgggcgccg agcgtgccgc accagcgcct gaccctgccg cgcgccgtgc    2220
tggcggcggc gaaggtgcag ctgctggcga tccagggcca gtccaagctg gccaccctga    2280
acgccgcgct ggcggtcgag gacgaacggc ggatgccggt tcgcgccttc ctccgcgcgc    2340
```

-continued

```
cgctgacgat ccattggtac ccctgagtgg cggactcgac tagtcaacgc catgagcggc    2400
ctcatttctt attctgagtt acaacagtcc gcaccgctgt ccggtagctc cttccggtgg    2460
gcgcggggca tgactatcgt cgccgcactt atgactgtct tctttatcat gcaactcgta    2520
ggacaggtgc cggcagcgcc caacagtccc ccggccacgg ggcctgccac catacccacg    2580
ccgaaacaag cgccctgcac cattatgttc cggatctgca tcgcaggatg ctgctggcta    2640
ccctgtggaa cacctacatc tgtattaacg aagcgctaac cgttttatc aggctctggg     2700 aggcagaata aatgatcata tcgtcaatta ttacctccac ggggagagcc tgagcaaact    2760
ggcctcaggc atttgagaag cacacggtca cactgcttcc ggtagtcaat aaaccggtaa    2820
accagcaata gacataagcg gctatttaac gaccctgccc tgaaccgacg accgggtcga    2880
atttgctttc gaatttctgc cattcatccg cttattatca cttattcagg cgtagcacca    2940
ggcgtttaag ggcaccaata actgccttaa aaaaattacg ccccgccctg ccactcatcg    3000
cagtactgtt gtaattcatt aagcattctg ccgacatgga agccatcaca gacggcatga    3060
tgaacctgaa tcgccagcgg catcagcacc ttgtcgcctt gcgtataata tttgcccatg    3120
gtgaaaacgg gggcgaagaa gttgtccata ttggccacgt ttaaatcaaa actggtgaaa    3180
ctcacccagg gattggctga gacgaaaaac atattctcaa taaacccttt agggaaatag    3240
gccaggtttt caccgtaaca cgccacatct tgcgaatata tgtgtagaaa ctgccggaaa    3300
tcgtcgtggt attcactcca gagcgatgaa aacgtttcag tttgctcatg gaaaacggtg    3360
taacaagggt gaacactatc ccatatcacc agctcaccgt ctttcattgc catacg        3416
```

<210> SEQ ID NO 10
<211> LENGTH: 157
<212> TYPE: PRT
<213> ORGANISM: HOMO SAPIENS

<400> SEQUENCE: 10

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
                20                  25                  30

Met Thr Asp Ser Asp Cys Arg Asp Asn Ala Pro Arg Thr Ile Phe Ile
            35                  40                  45

Ile Ser Met Tyr Lys Asp Ser Gln Pro Arg Gly Met Ala Val Thr Ile
        50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155

<210> SEQ ID NO 11
<211> LENGTH: 582
<212> TYPE: DNA
<213> ORGANISM: HOMO SAPIENS

-continued

<400> SEQUENCE: 11

```
atggctgctg aaccagtaga agacaattgc atcaactttg tggcaatgaa atttattgac    60
aatacgcttt actttatagc tgaagatgat gaaaacctgg aatcagatta ctttggcaag   120
cttgagagca aactatcggt cattcgtaat ttaaatgacc aggtcctatt tatcgaccaa   180
gggaatcgtc cactattcga ggacatgaca acagtgact gccgagacaa tgcgccgcga    240
accattttca ttatatctat gtacaaggat tctcagccgc gcggaatggc cgtaactatt   300
tctgtcaaat gtgaaaagat atccacgctg tcgtgtgaga acaagattat tagtttcaaa   360
gagatgaatc cgccggataa tatcaaggac acgaagtctg atatcatatt tttccagcgc   420
agcgtgccgg ggcacgataa caagatgcaa tttgaatcat ccagctatga agggtacttt   480
cttgcatgcg agaaggaacg cgatctcttt aaacttattt taaagaaaga ggacgagcta   540
ggcgatcgca gcattatgtt cactgtccaa aatgaagact ag                      582
```

<210> SEQ ID NO 12
<211> LENGTH: 849
<212> TYPE: DNA
<213> ORGANISM: HOMO SAPIENS

<400> SEQUENCE: 12

```
atgggccatc atcatcatca tcatggcata ctcaaacttt gtcctcgtga agaattcctg    60
agactgtgta aaaaaaatca tgatgagatc tatccaataa aaagagaga ggaccgcaga   120
cgcctggctc tcatcatatg caatacaaag tttgatcacc tgcctgcaag gaatggggct   180
cactatgaca tcgtggggat gaaaaggctg cttcaaggcc tgggctacac tgtggttgac   240
gaaaagaatc tcacagccag ggatatggag tcagtgctga gggcatttgc tgccagacca   300
gagcacaagt cctctgacag cacgttcttg gtactcatgt ctcatggcat cctagaggga   360
atctgcggaa ctgcgcataa aaagaaaaaa ccggatgtgc tgctttatga caccatcttc   420
cagatattca acaaccgcaa ctgcctcagt ctaaaggaca aacccaaggt catcattgtc   480
caggcctgca gaggtgaaaa acatggggaa ctctgggtca gagactctcc agcatccttg   540
gcagtcatct cttcacagtc atctgagaac ctggaggcag attctgtttg caagatccac   600
gaggagaagg acttcattgc tttctgttct tcaacaccac ataacgtgtc ctggagagac   660
cgcacaaggg gctccatctt cattacgaaa ctcatcacat gcttccagaa atattcttgc   720
tgctgccacc taatggaaat atttcggaag gtacagaaat catttgaagt tccacaggct   780
aaagcccaga tgcccaccat agaacagca accttgacaa gagatttcta cctctttcct   840
ggcaattga                                                          849
```

<210> SEQ ID NO 13
<211> LENGTH: 6687
<212> TYPE: DNA
<213> ORGANISM: Artificial Sequence
<220> FEATURE:
<223> OTHER INFORMATION: Comprised of pET Vector and Homo Sapien

<400> SEQUENCE: 13

```
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
ctttctcgcc acgttcgccg gctttccccg tcaagctcta aatcggggc tccctttagg    180
gttccgattt agtgctttac ggcacctcga ccccaaaaaa cttgattagg gtgatggttc   240
acgtagtggg ccatcgccct gatagacggt ttttcgccct ttgacgttgg agtccacgtt   300
```

```
ctttaatagt ggactcttgt tccaaactgg aacaacactc aaccctatct cggtctattc      360
ttttgattta taagggattt tgccgatttc ggcctattgg ttaaaaaatg agctgattta      420
acaaaaattt aacgcgaatt ttaacaaaat attaacgttt acaatttcag gtggcacttt      480
tcggggaaat gtgcgcggaa ccccatttgt tttattttc taaatacatt caaatatgta      540
tccgctcatg aattaattct tagaaaaact catcgagcat caaatgaaac tgcaatttat      600
tcatatcagg attatcaata ccatattttt gaaaaagccg tttctgtaat gaaggagaaa      660
actcaccgag gcagttccat aggatggcaa gatcctggta tcggtctgcg attccgactc      720
gtccaacatc aatacaacct attaatttcc cctcgtcaaa aataaggtta tcaagtgaga      780
aatcaccatg agtgacgact gaatccggtg agaatggcaa aagtttatgc atttctttcc      840
agacttgttc aacaggccag ccattacgct cgtcatcaaa atcactcgca tcaaccaaac      900
cgttattcat tcgtgattgc gcctgagcga gacgaaatac gcgatcgctg ttaaaaggac      960
aattacaaac aggaatcgaa tgcaaccggc gcaggaacac tgccagcgca tcaacaatat     1020
tttcacctga tcaggatat tcttctaata cctggaatgc tgttttcccg gggatcgcag      1080
tggtgagtaa ccatgcatca tcaggagtac ggataaaatg cttgatggtc ggaagaggca     1140
taaattccgt cagccagttt agtctgacca tctcatctgt aacatcattg gcaacgctac     1200
ctttgccatg tttcagaaac aactctggcg catcgggctt cccatacaat cgatagattg     1260
tcgcacctga ttgcccgaca ttatcgcgag cccatttata cccatataaa tcagcatcca     1320
tgttggaatt taatcgcggc ctagagcaag acgtttcccg ttgaatatgg ctcataacac     1380
cccttgtatt actgtttatg taagcagaca gtttttattgt tcatgaccaa aatcccttaa     1440
cgtgagtttt cgttccactg agcgtcagac cccgtagaaa agatcaaagg atcttcttga     1500
gatccttttt ttctgcgcgt aatctgctgc ttgcaaacaa aaaaaccacc gctaccagcg     1560
gtggtttgtt tgccggatca agagctacca actcttttc cgaaggtaac tggcttcagc      1620
agagcgcaga taccaaatac tgtccttcta gtgtagccgt agttaggcca ccacttcaag     1680
aactctgtag caccgcctac atacctcgct ctgctaatcc tgttaccagt ggctgctgcc     1740
agtggcgata agtcgtgtct taccgggttg gactcaagac gatagttacc ggataaggcg     1800
cagcggtcgg gctgaacggg gggttcgtgc acacagccca gcttggagcg aacgacctac     1860
accgaactga gatacctaca gcgtgagcta tgagaaagcg ccacgcttcc cgaagggaga     1920
aaggcggaca ggtatccggt aagcggcagg gtcggaacag gagagcgcac gagggagctt     1980
ccagggggaa acgcctggta tctttatagt cctgtcgggt ttcgccacct ctgacttgag     2040
cgtcgatttt tgtgatgctc gtcagggggg cggagcctat ggaaaaacgc cagcaacgcg     2100
gcctttttac ggttcctggc cttttgctgg ccttttgctc acatgttctt tcctgcgtta     2160
tcccctgatt ctgtggataa ccgtattacc gcctttgagt gagctgatac cgctcgccgc     2220
agccgaacga ccgagcgcag cgagtcagtg agcgaggaag cggaagagcg cctgatgcgg     2280
tattttctcc ttacgcatct gtgcggtatt tcacaccgca tatatggtgc actctcagta     2340
caatctgctc tgatgccgca tagttaagcc agtatacact ccgctatcgc tacgtgactg     2400
ggtcatggct gcgccccgac acccgccaac acccgctgac gcgccctgac gggcttgtct     2460
gctcccggca tccgcttaca gacaagctgt gaccgtctcc gggagctgca tgtgtcagag     2520
gttttcaccg tcatcaccga aacgcgcgag gcagctgcgg taaagctcat cagcgtggtc     2580
gtgaagcgat tcacagatgt ctgcctgttc atccgcgtcc agctcgttga gtttctccag     2640
aagcgttaat gtctggcttc tgataaagcg ggccatgtta agggcggttt tttcctgttt     2700
```

```
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtcccgga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaccaca    5040
ccttaaggag gatataacat atggctgctg aaccagtaga agacaattgc atcaactttg    5100
```

```
tggcaatgaa atttattgac aatacgcttt actttatagc tgaagatgat gaaaacctgg    5160
aatcagatta ctttggcaag cttgagagca aactatcggt cattcgtaat ttaaatgacc    5220
aggtcctatt tatcgaccaa gggaatcgtc cactattcga ggacatgaca gacagtgact    5280
gccgagacaa tgcgccgcga accatttca ttatatctat gtacaaggat tctcagccgc     5340
gcggaatggc cgtaactatt tctgtcaaat gtgaaaagat atccacgctg tcgtgtgaga    5400
acaagattat tagtttcaaa gagatgaatc cgccggataa tatcaaggac acgaagtctg    5460
atatcatatt tttccagcgc agcgtgccgg ggcacgataa caagatgcaa tttgaatcat    5520
ccagctatga agggtacttt cttgcatgcg agaaggaacg cgatctcttt aaacttattt    5580
taaagaaaga ggacgagcta ggcgatcgca gcattatgtt cactgtccaa aatgaagact    5640
agtggaggat ataataccag gaataaataa aatccatggg ccatcatcat catcatcatg    5700
gcatactcaa actttgtcct cgtgaagaat tcctgagact gtgtaaaaaa aatcatgatg    5760
agatctatcc aataaaaaag agagaggacc gcagacgcct ggctctcatc atatgcaata    5820
caaagtttga tcacctgcct gcaaggaatg gggctcacta tgacatcgtg gggatgaaaa    5880
ggctgcttca aggcctgggc tacactgtgg ttgacgaaaa gaatctcaca gccagggata    5940
tggagtcagt gctgagggca tttgctgcca gaccagagca caagtcctct gacagcacgt    6000
tcttggtact catgtctcat ggcatcctag agggaatctg cggaactgcg cataaaaaga    6060
aaaaaccgga tgtgctgctt tatgacacca tcttccagat attcaacaac cgcaactgcc    6120
tcagtctaaa ggacaaaccc aaggtcatca ttgtccaggc ctgcagaggt gaaaaacatg    6180
gggaactctg ggtcagagac tctccagcat ccttggcagt catctcttca cagtcatctg    6240
agaacctgga ggcagattct gtttgcaaga tccacgagga gaaggacttc attgcttttct   6300 gttcttcaac accacataac gtgtcctgga gagaccgcac aaggggctcc atcttcatta    6360
cggaactcat cacatgcttc cagaaatatt cttgctgctg ccacctaatg gaaatatttc    6420
ggaaggtaca gaaatcattt gaagttccac aggctaaagc ccagatgccc accatagaac    6480
gagcaacctt gacaagagat ttctacctct ttcctggcaa ttgactcgag caccaccacc    6540
accaccactg agatccggct gctaacaaag cccgaaagga agctgagttg gctgctgcca    6600
ccgctgagca ataactagca taaccccttg gggcctctaa acgggtcttg aggggttttt    6660
tgctgaaagg aggaactata tccggbt                                        6687
```

<210> SEQ ID NO 14
<211> LENGTH: 7454
<212> TYPE: DNA
<213> ORGANISM: Artificial Sequence
<220> FEATURE:
<223> OTHER INFORMATION: Comprised of pET Vector & Homo Sapien,
      Pseudomones Aeruginosa

<400> SEQUENCE: 14

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcgggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta taagggattt tgccgatttc ggcctattgg ttaaaaaatg agctgattta     420
acaaaaattt aacgcgaatt ttaacaaaat attaacgttt acaatttcag gtggcacttt     480
```

```
tcggggaaat gtgcgcggaa cccctatttg tttattttc taaatacatt caaatatgta      540
tccgctcatg aattaattct tagaaaaact catcgagcat caaatgaaac tgcaatttat      600
tcatatcagg attatcaata ccatattttt gaaaaagccg tttctgtaat gaaggagaaa      660
actcaccgag gcagttccat aggatggcaa gatcctggta tcggtctgcg attccgactc      720
gtccaacatc aatacaacct attaatttcc cctcgtcaaa ataaggttta tcaagtgaga      780
aatcaccatg agtgacgact gaatccggtg agaatggcaa aagtttatgc atttctttcc      840
agacttgttc aacaggccag ccattacgct cgtcatcaaa atcactcgca tcaaccaaac      900
cgttattcat tcgtgattgc gcctgagcga gacgaaatac gcgatcgctg ttaaaaggac      960
aattacaaac aggaatcgaa tgcaaccggc gcaggaacac tgccagcgca tcaacaatat     1020
tttcacctga atcaggatat tcttctaata cctggaatgc tgttttcccg gggatcgcag     1080
tggtgagtaa ccatgcatca tcaggagtac ggataaaatg cttgatggtc ggaagaggca     1140
taaattccgt cagccagttt agtctgacca tctcatctgt aacatcattg gcaacgctac     1200
ctttgccatg tttcagaaac aactctggcg catcgggctt cccatacaat cgatagattg     1260
tcgcacctga ttgcccgaca ttatcgcgag cccatttata cccatataaa tcagcatcca     1320
tgttggaatt taatcgcggc ctagagcaag acgtttcccg ttgaatatgg ctcataacac     1380
cccttgtatt actgtttatg taagcagaca gtttttattgt tcatgaccaa aatcccttaa     1440
cgtgagtttt cgttccactg agcgtcagac cccgtagaaa agatcaaagg atcttcttga     1500
gatccttttt ttctgcgcgt aatctgctgc ttgcaaacaa aaaaaccacc gctaccagcg     1560
gtggtttgtt tgccggatca agagctacca actctttttc cgaaggtaac tggcttcagc     1620
agagcgcaga taccaaatac tgtccttcta gtgtagccgt agttaggcca ccacttcaag     1680
aactctgtag caccgcctac atacctcgct ctgctaatcc tgttaccagt ggctgctgcc     1740
agtggcgata agtcgtgtct taccgggttg gactcaagac gatagttacc ggataaggcg     1800
cagcggtcgg gctgaacggg gggttcgtgc acacagccca gcttggagcg aacgacctac     1860
accgaactga gatacctaca gcgtgagcta tgagaaagcg ccacgcttcc gaagggaga     1920
aaggcggaca ggtatccggt aagcggcagg gtcggaacag gagagcgcac gagggagctt     1980
ccaggggaa acgcctggta tctttatagt cctgtcgggt ttcgccacct ctgacttgag     2040
cgtcgatttt tgtgatgctc gtcaggggg cggagcctat ggaaaaacgc cagcaacgcg     2100
gccttttac ggttcctggc cttttgctgg ccttttgctc acatgttctt tcctgcgtta     2160
tcccctgatt ctgtggataa ccgtattacc gcctttgagt gagctgatac cgctcgccgc     2220
agccgaacga ccgagcgcag cgagtcagtg agcgaggaag cggaagagcg cctgatgcgg     2280
tatttttctcc ttacgcatct gtgcggtatt tcacaccgca tatatggtgc actctcagta     2340
caatctgctc tgatgccgca tagttaagcc agtatacact ccgctatcgc tacgtgactg     2400
ggtcatggct gcgccccgac acccgccaac acccgctgac gcgccctgac gggcttgtct     2460
gctcccggca tccgcttaca gacaagctgt gaccgtctcc gggagctgca tgtgtcagag     2520
gttttcaccg tcatcaccga aacgcgcgag gcagctgcgg taaagctcat cagcgtggtc     2580
gtgaagcgat tcacagatgt ctgcctgttc atccgcgtcc agctcgttga gtttctccag     2640
aagcgttaat gtctggcttc tgataaagcg ggccatgtta agggcggttt tttcctgttt     2700
ggtcactgat gcctccgtgt aagggggatt tctgttcatg ggggtaatga taccgatgaa     2760
acgagagagg atgctcacga tacgggttac tgatgatgaa catgcccggt tactggaacg     2820
ttgtgagggt aaacaactgg cggtatggat gcggcgggac cagagaaaaa tcactcaggg     2880
```

```
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag gtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg cgcgcattg    3840 cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccgaaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg cgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaccaca    5040
ccttaaggag gatataacat atggctgctg aaccagtaga agacaattgc atcaactttg    5100 tgcaatgaa atttattgac aatacgcttt actttatagc tgaagatgat gaaaacctgg    5160
aatcagatta ctttggcaag cttgagagca aactatcggt cattcgtaat ttaaatgacc    5220
aggtcctatt tatcgaccaa gggaatcgtc cactattcga ggacatgaca gacagtgact    5280
```

```
gccgagacaa tgcgccgcga accattttca ttatatctat gtacaaggat tctcagccgc   5340
gcggaatggc cgtaactatt tctgtcaaat gtgaaaagat atccacgctg tcgtgtgaga   5400
acaagattat tagtttcaaa gagatgaatc cgccggataa tatcaaggac acgaagtctg   5460
atatcatatt tttccagcgc agcgtgccgg ggcacgataa caagatgcaa tttgaatcat   5520
ccagctatga agggtacttt cttgcatgcg agaaggaacg cgatctcttt aaacttattt   5580
taaagaaaga ggacgagcta ggcgatcgcg gcattatgtt cactgtccaa aatgaagact   5640
agtggaggat ataataccag gaataaataa aatccatggg ccatcatcat catcatcatg   5700
gcatactcaa actttgtcct cgtgaagaat tcctgagact gtgtaaaaaa aatcatgatg   5760
agatctatcc aataaaaaag agagaggacc gcagacgcct ggctctcatc atatgcaata   5820
caaagtttga tcacctgcct gcaaggaatg gggctcacta tgacatcgtg gggatgaaaa   5880
ggctgcttca aggcctgggc tacactgtgg ttgacgaaaa gaatctcaca gccagggata   5940
tggagtcagt gctgagggca tttgctgcca gaccagagca caagtcctct gacagcacgt   6000
tcttggtact catgtctcat ggcatcctag agggaatctg cggaactgcg cataaaaaga   6060
aaaaaccgga tgtgctgctt tatgacacca tcttccagat attcaacaac cgcaactgcc   6120
tcagtctaaa ggacaaaccc aaggtcatca ttgtccaggc ctgcagaggt gaaaaacatg   6180
gggaactctg ggtcagagac tctccagcat ccttggcagt catctcttca cagtcatctg   6240
agaacctgga ggcagattct gtttgcaaga tccacgagga gaaggacttc attgctttct   6300
gttcttcaac accacataac gtgtcctgga gagaccgcac aaggggctcc atcttcatta   6360
cggaactcat cacatgcttc cagaaatatt cttgctgctg ccacctaatg gaaatatttc   6420
ggaaggtaca gaaatcattt gaagttccac aggctaaagc ccagatgccc accatagaac   6480
gagcaacctt gacaagagat ttctacctct ttcctggcaa ttgactcgag ctcggtggcc   6540
ctggtggccc gcgatgggag gagttggtat ggcgatttct gagttgaagc tgccggccgg   6600
cgtcggcctg caggtctggg gcagcgccgc cgagcaggcc cgcggcctgg ccgccgaggt   6660
cgccggccgg ttgcgctcgg cgctggccga gcagggccag gcgctgctgg tggtgtccgg   6720
tgggcgcagt ccggtggcct tcctcgaagc cttgagcgag gagccgctgg actggtcgcg   6780
gatcacagtc agcctggccg acgagcgctg ggtgccggag tcgcatgccg atagcaacgc   6840
cggcctggtt cgccgccacc tgctccgtgg cgaggcggcg aaggcgcgct tcatcggcct   6900
ctaccagccg gcggcgagcc tggaggaagc ggccgagctg gccgaccatc acctgcacga   6960
gctgccattg ccgatcgacg tgctggtcct cggcatgggc gacgacggcc ataccgcctc   7020
gctgttcccg aacagccctg gcctggacct ggcgatggat ccccagggga cgcgccgttg   7080
cctgccgatg tgggcgccga gcgtgccgca ccagcgcctg accctgccgc gcgccgtgct   7140
ggcggcggcg aaggtgcagc tgctggcgat ccagggccag tccaagctgg ccaccctgaa   7200
cgccgcgctg gcggtcgagg acgaacggcg gatgccggtt cgcgccttcc tccgcgcgcc   7260
gctgacgatc cattggtacc cctgagtggc ggactcgagc accaccacca ccaccactga   7320
gatccggctg ctaacaaagc ccgaaaggaa gctgagttgg ctgctgccac cgctgagcaa   7380
taactagcat aaccccttgg ggcctctaaa cgggtcttga ggggtttttt gctgaaagga   7440
ggaactatat ccgg                                                    7454
```

METHODS FOR REDUCING GLUCONOYLATION OF PROTEINS

This application is a 371 National Phase entry of international application number PCT/US04/06507, filed Mar. 4, 2004 which claims priority to U.S. Ser. No. 60/451,686 filed Mar. 4, 2003.

FIELD OF THE INVENTION

This invention is in the field of biochemical engineering. More particularly, this invention relates to fermentation processes for producing polypeptides.

BACKGROUND OF THE INVENTION

*Escherichia coli* ("*E. coli*") is a commonly used host for expression of proteins for research, diagnostic, therapeutic, and industrial purposes. Modern expression systems are capable of achieving high levels of a wide variety of proteins (Baneyx, *Current Opinion in Biotechnology* 10:411-421 (1999)). However, the quality of the expressed protein is often as important or more important than quantity. Proteins expressed in *E. coli* may be formed as insoluble aggregates, or they may have misincorporated amino acids (Bogosian, et al., *Journal of Biological Chemistry* 264:531-539 (1989)) or retain the N-terminal methionine (Chaudhuri, et al., *Journal of Molecular Biology* 285:1179-1194 (1999); Vassileva-Atanassova, et al, *Journal of Biotechnology* 69:63-67 (1999); Yamashita, et al., *Protein Expression & Purification* 16:47-52 (1999)). In addition, undesired post-translational modifications may occur such as oxidation (Berti, et al., *Protein Expression & Purification* 11:111-118 (1997); Konz, et al., *Biotechnology Progress* 14:393-409 (1998)) or α-N-6-phosphogluconoylation (Geoghegan, et al., *Anal. Biochem.* 267: 169-184 (1999); Kim et al., *Acta Crystallographica* Section D-Biological Crystallography 57:759-762 (2001); Yan, et al. *Biochemical & Biophysical Research Communications* 262: 793-800 (1999) "Yan et al. I;" Yan, et al., *Biochemical & Biophysical Research Communications* 259:271-282 (1999) "Yan et al. II"). These modifications may adversely effect activity, stability, structure, or immunogenicity of the expressed protein, greatly reducing the utility of *E. coli* as a host for polypeptide expression.

Alpha(α)-N-6-phosphogluconoylation of several recombinant proteins fused to hexahistidine affinity tags ("hexa His-tag") has been described (Geoghegan, et al; Kim, et al.; Yan et al. I; Yan et al. II). In these studies, a gluconic acid derivative was found to attach to the end terminus of the recombinant protein. All of these proteins were expressed in B strains of *E. coli* using pET-based vectors (Novagen). Where reported, LB medium was used. The adduct was detected as an extra mass associated with the polypeptide of either 258 Daltons ("Da"), representing the addition of 6-phosphogluconolactone (6-PGL), or 178 Da, representing the presence of gluconolactone without the phosphate. Phosphogluconoylation was presumed to occur at the N-terminal α-amino group through reaction with endogenous 6-PGL, an intermediate of the pentose phosphate shunt. The +178 Da adduct was proposed to be the result of enzymatic activity acting on the +258 Da adduct to remove the phosphate. Formation of the adduct was shown to be specific to the amino acid sequence at the N-terminus adjacent to the His-tag. Polypeptide sequences of GXXHHHH, where XX is SS, SA, AS, or AA, were the most prone to α-N-6-phosphogluconoylation, whereas SHHHHHH was less prone, and PHHHHHH and PFHHHHHH were not modified at all (Geoghegan, et al.). Modifications at other amino groups elsewhere on the protein were not detected in vivo or in in vitro experiments that used high levels of added gluconolactone. (Geoghegan, et al.)

N-terminal phosphogluconoylation has been shown to inhibit crystallization of proteins (Kim, et al.), but relatively little else is known about its effect on protein function, stability, or immunogenicity. It is expected that 6-PGL, being a potent electrophile, may be involved in glycation reactions in vivo (Rakitzis and Papandreou, *Chemico-Biological Interactions* 113:205-216 (1998)). Glycation of proteins has been widely studied and is known to play a major role in aging and disease states related to diabetic complications (Baynes and Monnier, *The Maillard Reaction in Aging, Diabetes, and Nutrition*. Alan R. Liss, New York (1989)). Exogenously added delta-gluconolactone has been shown to cause glycation of hemoglobin, which may be a factor in the vascular complications of diabetes (Lindsay, et al., *Clinica Chimica Acta* 263:239-247 (1997)). Furthermore, glycation of alanine aminotransferase at the epsilon-amino group of Lys313 markedly reduces its catalytic activity (Beranek, et al., *Molecular & Cellular Biochemistry* 218:35-39 (2001)).

6-Phosphogluconolactonase ("pgl") has been shown to be an essential enzyme of the pentose-phosphate pathway, specifically in the hydrolysis of 6-PGL to 6-phosphogluconic acid. (Miclet, et al., *J. Biol. Chem.* 276:34840-34846 (2001)) The gene encoding this enzyme has been identified in human (Collard, et al., FEBS Letters 459:223-226 (1999)), *Pseudomonas aeruginosa* (Hager, et al., *Journal of Bacteriology* 182:3934-3941 (2000)), and *Trypanosoma brucei* and *Plasmodium falciparum* (Miclet, et al.). Although pgl activity has long been observed in *E. coli* (Kupor and Fraenkel, *Journal of Bacteriology* 100:1296-1301 (1969) "Kupor I" and Kupor and Fraenkel, *Journal of Biological Chemistry* 247: 1904-1910 (1972) "Kupor II"), no gene sequence responsible for encoding an enzyme with this activity has been identified (Cordwell, S. *J. Arch. Microbiol.* 172:269-279 (1999)). It has been suggested that in addition to enabling metabolic flux through the pentose phosphate shunt, pgl activity inside the cell prevents accumulation of 6-PGL and consequential damaging reactions with intracellular nucleophiles (Miclet, et al.). Reported observations of phosphogluconoylation of proteins at the N-terminus supports the hypothesis that the 6-PGL produced in the pathway can modify proteins, but there has been no reported evidence that modulating pgl activity can affect the levels of modified protein.

Furthermore, *Escherichia coli* strain BL21 (DE3) is a commonly used host for expression of proteins for research, diagnostic, therapeutic, and industrial purposes Studier, F. W., and Moffatt, B. A., *J. Mol. Biol.* 1986 May 5; 189(1):113-130. This strain is commercially attractive because it achieves very high expression levels of recombinant protein by means of coupling expression of a chromosomal copy of the T7 RNA polymerase and the use of a plasmid based T7 RNA polymerase promoter on the recombinant protein of interest. Accordingly, since the 17 RNA polymerase is an extremely selective and active RNA polymerase, transcription of the recombinant protein accumulate to very high levels, often even to the extent that host cell transcripts are diminished.

Unfortunately, the strain BL21 (DE3) releases very low, yet detectable, infectious lambda phage particles on the order of 10-20 plaque forming units/ml (PFU), Stewart Shuman, *Proc. Natl. Acad. Sci. USA* 1989; 89:3489-3493. Apparently, the T7 RNA polymerase gene was introduced into the BL21 host cell chromosome by transduction with the defective lambda phage DE3 carrying the T7 RNA polymerase gene inserted into the lambda int gene Studier, F. W., and Moffatt, B. A., *J. Mol. Biol.* 1986; 189(1):113-130. The resulting defective prophage cannot replicate normally due to the int gene interruption. Chromosomal excision of the DE3 prophage is a requirement for, the replication of the prophage prior to packaging and release of infectious phage particles and is dependant on homologous excisional recombination that is directed by the product of the int gene. As described herein very low levels of phage particles released are due to abnormal, int independent random prophage excision events. While the release of low levels of infectious phage particles may be acceptable in some research laboratories, any release of infectious phage is totally unacceptable in the biopharmaceuticals manufacturing plant setting both because of considerations for patient safety and because release of infectious agents can put at risk other *E. coli* based manufacturing processes.

A method for expressing or overexpressing polypeptides in a microorganism, such as *E. coli*, with a reduced incidence of phosphogluconoylation during fermentation is greatly needed. In addition, creation of a totally phage free BL21 (DE3) host cell would be highly desirable for the manufacture of therapeutic recombinant proteins in the *E. coli* format.

SUMMARY OF THE INVENTION

The present invention provides methods for preventing gluconoylation of polypeptides expressed by microorganisms by growing the microorganism in rich culture medium.

The present invention also provides methods for preventing gluconoylation of polypeptides expressed by microorganisms that include introducing (e.g., transforming, infecting or transfecting) DNA encoding a polypeptide that demonstrates pgl activity into the microorgansim. This polypeptide may be a phosphogluconolactonase enzyme. In another aspect of the invention, the phosphogluconolactonase enzyme may have an amino acid sequence having at least 90% sequence identity to the phosphogluconolactonase enzyme produced by *Pseudomonas*, including but to limited to, *P. aeruginosa.*

The present invention also provides microorganisms capable of preventing gluconoylation of proteins. In one embodiment, a microorganism may contain DNA encoding a polypeptide that demonstrates pgl activity.

The present invention also provides an isolated polynucleotide that has at least 90% identity to the polynucleotide set forth in SEQ ID NO:7.

The present invention also provides a microorgansim free of detectable infectious lambda phage expression.

BRIEF DESCRIPTION OF THE FIGURES

FIG. 2 shows a polynucleotide sequence for vector pECO-1-pgl-2-13. (SEQ ID NO:9)

FIG. 4 shows a polynucleotide sequence for vector pET28ProIL18Casp5. (SEQ ID NO:13)

FIG. 6 shows a polynucleotide sequence for vector pET28proIL18casp5+pgl (SEQ ID NO:14).

FIG. 7 shows a polynucleotide sequence, SEQ ID NO:7.

FIG. 8 shows a polypeptide sequence, SEQ ID NO:8.

GLOSSARY

Figure 1:
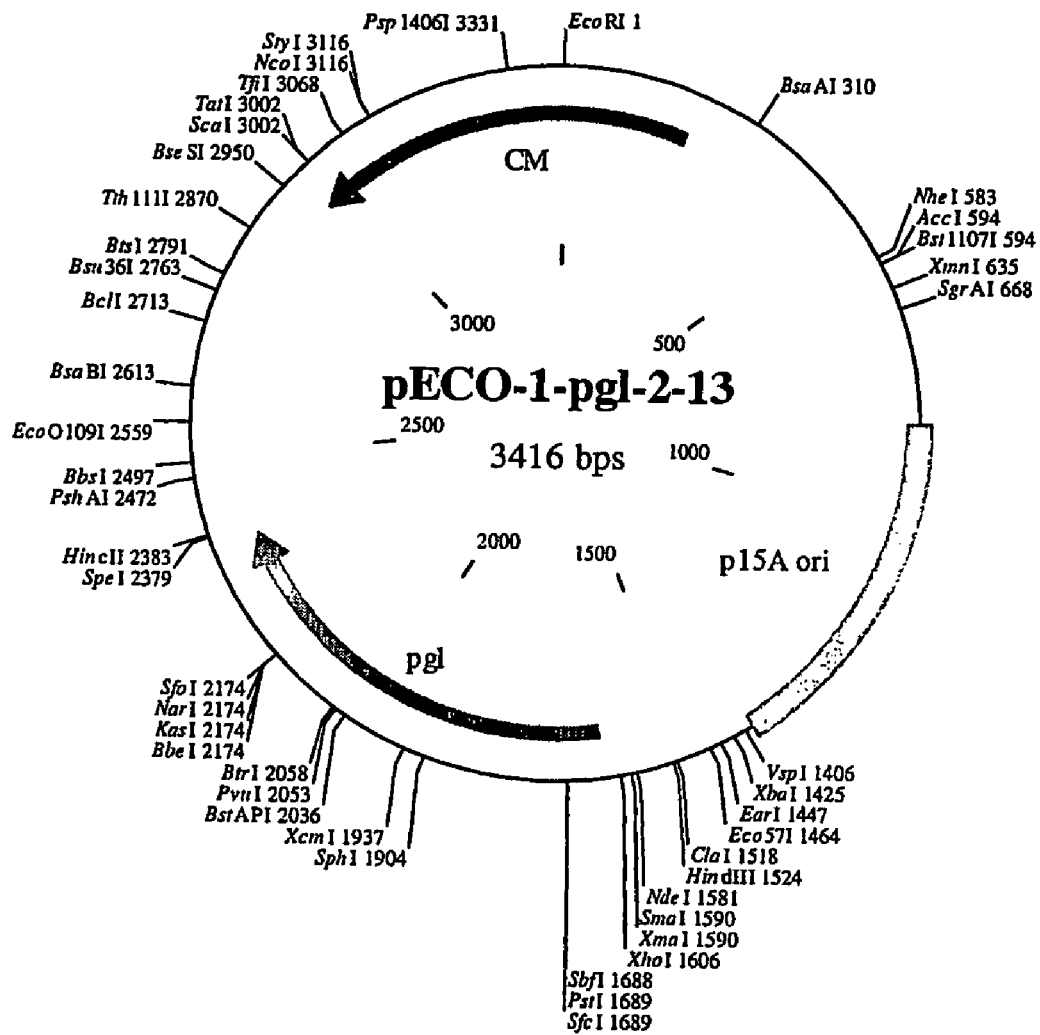
FIG. 1 shows a restriction enzyme map of vector pECO-1-pgl-2-13.
Figure 3:
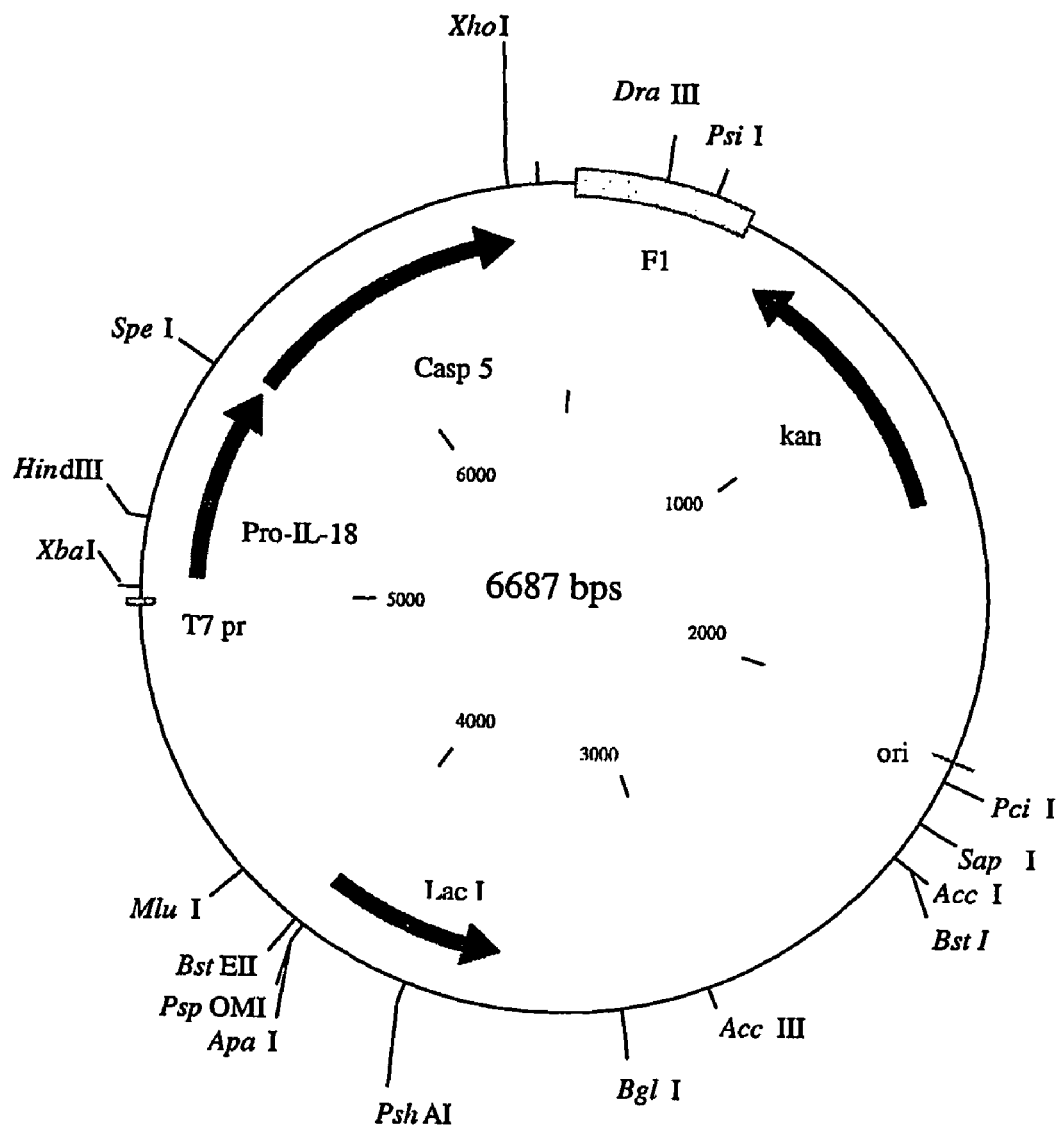
FIG. 3 shows a restriction enzyme map of vector pET28ProIL18Casp5.
Figure 5:
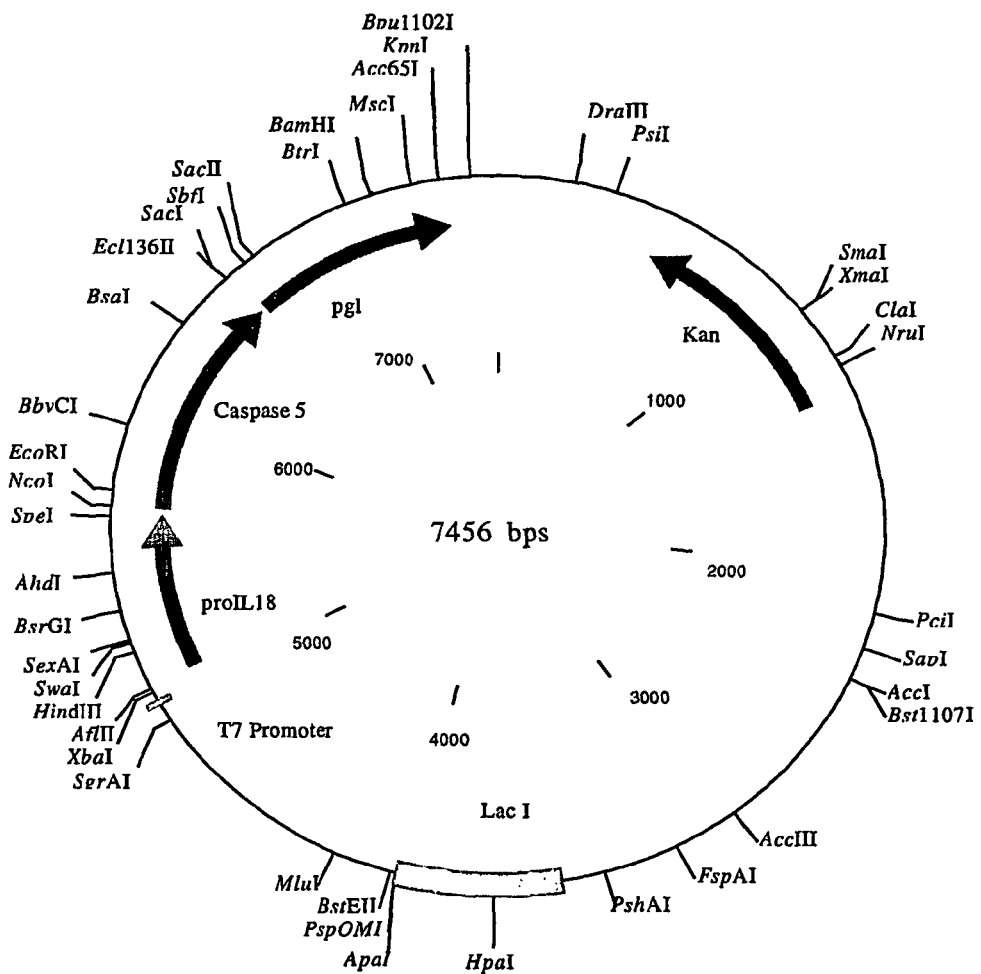
FIG. 5 shows a restriction enzyme map of vector pET28proIL18casp5+pgl.

"Host cell(s)" is a cell, including but not limited to a bacterial cell or cell of a microorganism, that has been introduced (e.g., transformed, infected or transfected) or is capable of introduction (e.g., transformation, infection or transfection) by an isolated polynucleotide sequence.

"Transformed" as known in the art, is the directed modification of an organism's genome or episome via the introduction of external DNA or RNA, or to any other stable introduction of external DNA or RNA.

"Transfected" as known in the art, is the introduction of external DNA or RNA into a microorganism, including but not limited to recombinant DNA or RNA.

"Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48:1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Altschul, S. F. et al., *J. Molec. Biol.* 215: 403-410 (1990). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403-410 (1990). The well known Smith Waterman algorithm may also be used to determine identity.

Parameters for polypeptide sequence comparison include the following:

Algorithm: Needleman and Wunsch, J. Mol. Biol. 48: 443-453 (1970)

Comparison matrix: BLOSSUM62 from Hentikoff and Hentikoff, Proc. Natl. Acad. Sci. USA. 89:10915-10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following:

Algorithm: Needleman and Wunsch, J. Mol. Biol. 48: 443-453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid comparisons.

A preferred meaning for "identity" for polynucleotides and polypeptides, as the case may be, are provided in (1) and (2) below.

(1) Polynucleotide embodiments further include an isolated polynucleotide comprising a polynucleotide sequence having at least a 70, 80, 85, 90, 95, 97 or 100% identity to the reference sequence of SEQ ID NO:7, wherein said polynucleotide sequence may be identical to the reference sequence of SEQ ID NO:7 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:7 by the integer defining the percent identity divided by 100 and then subtracting that product from said total number of nucleotides in SEQ ID NO:7, or:

$$n_n \leq x_n - (x_n \cdot y),$$

wherein $n_n$ is the number of nucleotide alterations, $x_n$ is the total number of nucleotides in SEQ ID NO:7, y is 0.95 for 95%, 0.97 for 97% or 1.00 for 100%, and · is the symbol for the multiplication operator, and wherein any non-integer product of $x_n$ and y is rounded down to the nearest integer prior to subtracting it from $x_n$. Alterations of a polynucleotide sequence encoding a polypeptide may create nonsense, missense or frameshift mutations in this coding sequence and thereby alter the polypeptide encoded by the polynucleotide following such alterations.

(2) Polypeptide embodiments further include an isolated polypeptide comprising a polypeptide having at least a 70, 80, 85, 90, 95, 97 or 100% identity to a polypeptide reference sequence, wherein said polypeptide sequence may be identical to the reference sequence or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids by the integer defining the percent identity divided by 100 and then subtracting that product from said total number of amino acids, or:

$$n_a \leq x_a - (x_a \cdot y),$$

wherein $n_a$ is the number of amino acid alterations, $x_a$ is the total number of amino acids in the sequence, y is 0.95 for 95%, 0.97 for 97% or 1.00 for 100%, and · is the symbol for the multiplication operator, and wherein any non-integer product of $x_a$ and y is rounded down to the nearest integer prior to subtracting it from $x_a$.

"Isolated"[1] means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", including but not limited to when such polynucleotide or polypeptide is introduced back into a cell.

"Polynucleotide(s)" generally refers to any polyribonucleotide or polydeoxyribonucleotide, that may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that comprise one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may comprise amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may comprise many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, PROTEINS—STRUCTURE AND MOLECULAR PROPERTIES, 2nd Ed., T. E. Creighton, W. H. Freeman and Company, New York (1993) and Wold, F., Posttranslational Protein Modifications: Perspectives and Prospects, pgs. 1-12 in POSTTRANSLATIONAL COVALENT MODIFICATION OF PROTEINS, B. C. Johnson, Ed., Academic Press, New York (1983); Seifter et al., Meth. Enzymol. 182:626-646 (1990) and Rattan et al., Protein Synthesis Posttranslational Modifications and Aging, Ann. N.Y. Acad. Sci. 663: 48-62 (1992). Polypeptides may be branched or cyclic, with or without branching. Cyclic, branched and branched circular polypeptides may result from post-translational natural processes and may be made by entirely synthetic methods, as well.

"Recombinant expression system(s)" refers to expression systems or portions thereof or polynucleotides of the invention introduced or transformed into a host cell or host cell lysate for the production of the polynucleotides and polypeptides of the invention.

"Variant(s)" as the term is used herein, is a polynucleotide, or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusion proteins and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. The present invention also includes include variants of each of the polypeptides of the invention, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5-10, 1-5, 1-3, 1-2 or 1 amino acids are substituted, deleted, or added in any combination. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

"Microorganism(s)" means a (i) prokaryote, including but not limited to, a member of the genus Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasturella, Moraxella, Acinetobacter, Erysipelothrix, Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia and Mycoplasma, and further including, but not limited to, a member of the species or group, Group A Streptococcus, Group B Streptococcus, Group C Streptococcus, Group D Streptococcus, Group G Streptococcus, Streptococcus pneumoniae, Streptococcus pyogenes, Streptococcus agalactiae, Streptococcus faecalis, Streptococcus faecium, Streptococcus durans, Neisseria gonorrheae, Neisseria meningitidis, Staphylococcus aureus, Staphylococcus epidermidis, Corynebacterium diptheriae, Gardnerella vaginalis, Mycobacterium tuberculosis, Mycobacterium bovis, Mycobacterium ulcerans, Mycobacterium leprae, Actinomyctes israeli, Listeria monocytogenes, Bordetella pertusis, Bordatella parapertusis, Bordetella bronchiseptica, Escherichia coli, Shigella dysenteriae, Haemophilus influenzae, Haemophilus aegyptius, Haemophilus parainfluenzae, Haemophilus ducreyi, Bordetella, Salmonella typhi, Citrobacter freundii, Proteus mirabills, Proteus vulgaris, Yersinia pestis, Kleibsiella pneumoniae, Serratia marcessens, Serratia liquefaciens, Vibrio cholera, Shigella dysenterii, Shigella flexneri, Pseudomonas aeruginosa, Franscisella tularensis, Brucella abortis, Bacillus anthracis, Bacillus cereus, Clostridium perfringens, Clostridium tetani, Clostridium botulinum, Treponema pallidum, Rickettsia rickettsii and Chlamydia trachomitis, (ii) an archaeon, including but not limited to Archaebacter, and (iii) a unicellular or filamentous eukaryote, including but not limited to, a protozoan, a fungus, a member of the genus Saccharomyces, Kluveromyces, or Candida, and a member of the species Saccharomyces ceriviseae, Kluveromyces lactis, or Candida albicans.

"Bacteria(um)(I)" means a (i) prokaryote, including but not limited to, a member of the genus Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasturella, Moraxella, Acinetobacter, Erysipelothrix, Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia and Mycoplasma, and further including, but not limited to, a member of the species or group, Group A Streptococcus, Group B Streptococcus, Group C Streptococcus, Group D Streptococcus, Group G Streptococcus, Streptococcus pneumoniae, Streptococcus pyogenes, Streptococcus agalactiae, Streptococcus faecalis, Streptococcus faecium, Streptococcus durans, Neisseria gonorrheae, Neisseria meningitidis, Staphylococcus aureus, Staphylococcus epidermidis, Corynebacterium diptheriae, Gardnerella vaginalis, Mycobacterium tuberculosis, Mycobacterium bovis, Mycobacterium ulcerans, Mycobacterium leprae, Actinomyctes israelii, Listeria monocytogenes, Bordetella pertusis, Bordatella parapertusis, Bordetella bronchiseptica, Escherichia coli, Shigella dysenteriae, Haemophilus influenzae, Haemophilus aegyptius, Haemophilus parainfluenzae, Haemophilus ducreyi, Bordetella, Salmonella typhi, Citrobacter freundii, Proteus mirabilis, Proteus vulgaris, Yersinia pestis, Kleibsiella pneumoniae, Serratia marcessens, Serratia liquefaciens, Vibrio cholera, Shigella dysenterii, Shigella flexneri, Pseudomonas aeruginosa, Franscisella tularensis, Brucella abortis, Bacillus anthracis, Bacillus cereus, Clostridium perfringens, Clostridium tetani, Clostridium botulinum, Tre-

*ponema pallidum, Rickettsia rickettsii* and *Chlamydia trachomitis*, and (ii) an archaeon, including but not limited to *Archaebacter.*

As used herein, "heterologous polypeptide(s)" refers to a polypeptide not naturally synthesized by a transformed host cell or microorganism of interest and introduced into the host cell or microorganism by recombinant DNA. For example, *E. coli* may act as a host microorganism for the expression of interleukin, which does not occur in non-transformed *E. coli*. Heterologous polypeptides may include polypeptides that have been modified to facilitate isolation.

As used herein "affinity tag" refers to any moiety associated with a molecule that may give said molecule a selective affinity for another substance or molecule. For instance, an affinity tag may be used to facilitate purification of a molecule by providing the molecule with a selective affinity for a column's packing material. A non-limiting example of an affinity tag is a his-tag.

As used herein, "His-tag" refers to a repeat of histidine amino acids and may include other amino acids encoded into a polypeptide through engineering techniques. Typically, a His-tag contains at least six ("hexa") histidine repeats and is located near the N-terminus of the polypeptide. His-tags can be used to facilitate purification of heterologous polypeptides over Ni-columns.

As used herein, "minimal medium" refers to cell growth medium comprising chemically defined ingredients including, but not limited to, buffers such as phosphate buffer, salts such as magnesium sulfate, calcium chloride, sodium chloride, or manganese sulfate, minerals such as iron, zinc, copper, cobalt, or molybendum, a carbon source such as glucose or glycerol, and a nitrogen source such as ammonium sulfate or nitrate. An example is M9 media (Kim, Y S, J H Seo and H Y Cha, *Enzyme and Microbial Technology* 33 (2003):460-465.)

As used herein, "rich medium" refers to cell growth medium comprising undefined ingredients and including, but not limited to, additional components such as buffers (for example phosphate buffer), salts (for example magnesium sulfate, calcium chloride, sodium chloride, or manganese sulfate), and a carbon source which may be glucose or glycerol, for example. The nitrogen source may be comprised of a protein hydrolysate such as yeast extract, meat hydrolysate, or soy hydrolysate. The nitrogen source may be provided at a concentration capable of supporting cell growth at a ratio of complex nitrogen source (in grams per liter) to maximum cell density (in OD units) of 1:1 or greater. Examples of rich medium include, but are not limited to, Superbroth (Atlas R M, Handbook of Microbiological Mesdia; Parks L C Ed.; CRC Press: Boca Raton Fla., pp. 281, 523, 529, 859), Teriffic Broth (Alpha Biosciences, Baltimore, Md. USA), Turbo Broth (Athena Enzyme Systems, Baltimore, Md. USA), or Hyper Broth (Athena Enzyme Systems, Baltimore, Md. USA).

As used herein, "gluconoylation" refers to the attachment of a gluconic acid derivative to a protein. Gluconoylation may include, but is not limited to, 6-phosphogluconolactone (6-PGL) adduct formation, acetylation, formylation, deformylation, gluconolactonation, or gluconic acid derivatization.

As used herein, "titer yield" refers to the concentration of a product (e.g., heterologously expressed polypeptide) in solution (e.g., culture broth or cell-lysis mixture or buffer) and it usually expressed as mg/L or g/L. An increase in titer yield may refer to an absolute or relative increase in the concentration of a product produced under two defined set of conditions.

As used herein, "pgl activity" refers to any activity of a 6-Phosphogluconolactonase ("pgl"). Such activity may include hydrolysis of 6-PGL to 6-phosphogluconic acid. Significant pgl activity may be defined as hydrolysis activity of at least 0.2 IU/min/g.

As herein used, the terms "stringent conditions" and a "stringent hybridization conditions" mean hybridization will occur only if there is at least 70% and preferably at least 80%, but especially preferably at least 95% identity between the sequences. An example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml denatured, sheared salmon sperm DNA, followed by washing the filters in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein, the disclosure of which is hereby incorporated in its entirety by reference.

DETAILED DESCRIPTION OF THE INVENTION

Cellular stresses arising from growth on minimal medium, high cell densities, and high-level heterologous polypeptide expression, among other stresses, may contribute to the gluconoylation of heterologous polypeptide. Alleviating one or more of these stressors may therefore affect the level of gluconoylation of protein expressed in the microorganism, which in turn may effect the purity and titer yield of a desired polypeptide. Some strains of *E. coli* may have higher levels of pgl activity than others (although the gene responsible for this activity has not been identified in *E. coli*. Cordwell, S. J. 1999. *Arch. Microbiol.* 172:269-279. Furthermore, gluconoylation of polypeptides may affect crystallization and structural determination of these polypeptides.

The present invention provides methods for preventing gluconoylation of a polypeptide expressed in a microorganism, comprising growing said microorganism in rich culture medium. In another aspect of the invention, the microorganism does not demonstrate significant 6-phosphogluconolactonase activity when grown in minimal medium. The microorganism may be a strain of *E. coli*. In another aspect of the invention, an *E. coli* is a B strain. In another aspect of the invention, a rich culture medium comprises a complex nitrogen source. A rich culture medium is capable of maintaining cell growth at ratio of 1:1 for concentration of complex nitrogen source to cell density. A complex nitrogen source may comprise tryptone, peptone, or yeast extract. In another aspect of the invention, a culture medium is Superbroth. Superbroth medium may be doubly concentrated. In another aspect of the invention, a microorganism is transfected with a recombinant DNA molecule encoding a heterologous polypeptide.

In another embodiment of the present invention, methods are provided for preventing gluconoylation of a polypeptide expressed in *E. coli* comprising fermenting a K strain variety of *E. coli* for the expression of the polypeptide. In another aspect of the invention, a K strain demonstrates at least about 100-fold higher phosphogluconolactonase activity compared with B strain grown under substantially the same conditions. In another aspect of the invention, a K strain is K-12.

In another embodiment of the present invention, methods are provided for preventing gluconoylation of polypeptides expressed in a microorganism, comprising introducing DNA into the microorganism, wherein the DNA encodes a polypeptide that demonstrates 6-phosphogluconolactonase activity. In another aspect of the invention, a microorgansim is E. coli. A DNA comprises DNA encoding a 6-phosphogluconolactonase enzyme. In another aspect of the invention, a DNA encoding a 6-phosphogluconolactonase enzyme has at least 70%, 80%, 85%, 90%, 95%, 97%, or 100% sequence identity to a DNA encoding 6-phosphogluconolactonase from a Pseudomonas, which may be P. aeruginosa. In another aspect of the invention, a DNA encoding a 6-phosphogluconolactonase enzyme has at least 70%, 80%, 85%, 90%, 95%, 97%, or 100% sequence identity to SEQ ID NO:7. In another aspect of the invention, a 6-phosphogluconolactonase enzyme has an amino acid sequence having at least 70%, 80%, 85%, 90%, 95%, 97%, or 100% sequence identity to SEQ ID NO:8. A DNA encoding a 6-phosphogluconolactonase enzyme comprises the sequence set forth in SEQ ID NO:7. DNA may be recombinant DNA, and/or it may be transformed into a genomic DNA of a microorganism.

In another embodiment of the present invention, a microorganism is provided that is capable of preventing gluconoylation of polypeptides. A microorganism comprises DNA that encodes a polypeptide that demonstrates 6-phosphogluconolactonase activity. A microorganism comprises DNA that encodes 6-phosphogluconolactonase. In another aspect of the invention, a DNA that encodes 6-phosphogluconolactonase has at least 70%, 80%, 85%, 90%, 95%, 97%, or 100% sequence identity to DNA encoding a 6-phosphogluconolactonase enzyme from a Pseudomonas and wherein the microorgansim is not Pseudomonas. In another aspect of the invention, a DNA that encodes 6-phosphogluconolactonase is from P. aeruginosa. In another aspect of the invention, a microorganism is a strain of E. coli. In another aspect of the invention, a microorganism is a strain of E. coli and the wherein a DNA that encodes 6-phosphogluconolactonase is incorporated into the genome of the microorganism.

In another embodiment of the present invention, an isolated polynucleotide is provided comprising a polynucleotide having at least a 70%, 80%, 85%, 90%, 95%, 97%, or 100% identity to the polynucleotide set forth in SEQ ID NO:7. In another aspect of the invention, an isolated polynucleotide comprises a polynucleotide having at least a 70%, 80%, 85%, 90%, 95%, 97%, or 100% sequence identity to a polynucleotide encoding a polypeptide comprising amino acids having at least 70%, 80%, 85%, 90%, 95%, 97%, or 100% sequence identity to SEQ ID NO:8. In another aspect of the invention, a DNA encodes a protein demonstrating 6-phosphogluconolactonase activity. In another aspect of the invention, a DNA sequence is set forth in SEQ ID NO:7. In another aspect of the invention, a DNA sequence is homologous to a DNA encoding 6-phosphogluconolactonase from P. aeruginosa. In another aspect of the invention, an isolated polynucleotide further comprises a polynucleotide that encodes a human interleukin-18, or variant thereof.

In another embodiment of the present invention, methods are provided for improving polypeptide crystal formation comprising expressing said polypeptide by a method of the invention in order to reduce glyconoylation of the polypeptide.

In another embodiment of the present invention, methods are provided for improving growth efficiency and expression of a polypeptide in a microorganism. In one aspect, a polypeptide demonstrates an increased titer yield at fermentation stage compared with gluconoylated polypeptide.

In another embodiment of the present invention, methods are provided for producing a human interleukin comprising co-expressing said human interleukin in a microorganism with an enzyme having 6-Phosphogluconolactonase ("pgl") activity. In one aspect, a human interleukin is an IL-18 protein, or variant thereof. In one aspect, a microorgansim is E. coli. In one aspect, the pgl is encoded by a polynucleotide that is transformed or transfected into the E. coli, including but not limited to being transformed into the genome or episome.

In another embodiment of the present invention, methods are provided producing a human interleukin comprising expressing the human interleukin in a microorganism that is grown in a rich culture medium. In one aspect, a human interleukin is IL-18 protein, or a variant thereof. In one aspect, the microorgansim is E. coli. In one aspect, a rich culture medium comprises phytone peptone. In one aspect, a rich culture medium comprises bacto yeast extract.

In another embodiment of the present invention, a microorgansim free of detectable infectious lambda phage expression is provided. In one aspect, lambda phage capsid structural protein, gpE, is deleted or disrupted within a microorganism. Deletion or disruption of a protein can be achieved in several non-limiting ways. A gene encoding a protein may be either partially or completely removed from a microorganism. A gene encoding a protein can be genetically modified by such non-limiting techniques as point mutation or random mutation. A protein may be cleaved or modified chemically or enzymatically to disrupt its structure or function. A promoter regulating gene expression can be disrupted or deleted to eliminate or reduce gene expression. Solution conditions or temperature can be regulated to effect protein structure or function. In one aspect, a microorganism is an E. coli. In another aspect a microorganism comprises a T7 RNA polymerase gene.

The following examples illustrate various aspects of this invention. These examples do not limit the scope of this invention which is defined by the appended claims.

EXAMPLES

Example 1

An improved strain of E. coli BL21 (DE3) strain was created that is free of detectable infectious lambda phage expression by knocking out a major lambda phage capsid structural protein gpE. This strain was used in the Examples presented herein.

A 413 base pair internal fragment of the gpE coding region was PCR amplified using the primer pair:

```
5' AGCTGGCCATTGCTCAGGTCGAAG 3'    (SEQ ID NO: 1)

5' GTACTGTCCGGAATACACGACGATG 3'   (SEQ ID NO: 2)
``` and BL21 (DE3) chromosomal DNA as template. The resulting fragment:

```
                                             (SEQ ID NO: 3)
AGCTGGCCAT TGCTCAGGTC GAAGAGATGC AGGCAGTTTC

TGCCGTGCTT AAGGGCAAAT ACACCATGAC CGGTGAAGCC

TTCGATCCGG TTGAGGTGGA TATGGGCCGC AGTGAGGAGA

ATAACATCAC GCAGTCCGGC GGCACGGAGT GGAGCAAGCG

TGACAAGTCC ACGTATGACC CGACCGACGA TATCGAAGCC

TACGCGCTGA ACGCCAGCGG TGTGGTGAAT ATCATCGTGT

TCGATCCGAA AGGCTGGGCG CTGTTCCGTT CCTTCAAAGC
```

-continued

```
CGTCAAGGAG AAGCTGGATA CCCGTCGTGG CTCTAATTCC

GAGCTGGAGA CAGCGGTGAA AGACCTGGGC AAAGCGGTGT

CCTATAAGGG GATGTATGGC GATGTGGCCA TCGTCGTGTA

TTCCGGACAG TAC
```

PCR amplification product was TA cloned and sequence verified using standard techniques. Next, a functional copy of a chloramphenicol resistance gene was introduced into the EcoRV site centrally located and shown bolded in the cloned gpE sequence. The chloramphenicol interrupted gpE fragment construct was then used as a linear homologous recombination knock-out vector for the genetic knock-out of the lambda (DE3) gpE gene residing in E. coli host strain BL21 (DE3). This knock-out vector was introduced into the host cell exactly as described by Kirill A. Datsenko and Barry Wanner, *Proc. Natl. Acad. Sci. USA* 2000; 97:6640-6645, except the vector described herein was used. Putative gpE knock-outs were preliminarily identified by the ability to grow in the presence of 6 μg/ml chloramphenicol, and were subsequently confirmed by PCR analysis. One such gpE knock-out of BL21 (DE3) was banked and given the GSK designation ECC-023.

ECC-023 was tested for the presence of infectious phage particles in the very sensitive plaque assay. As shown in Table 1, the parental BL21 (DE3) expressed barely detectable amounts of phage when not induced to do so, approximately 20 pfu, but nearly three orders of magnitude more when induced by the SOS response to genetic damage (UV irradiation). The gpE knock-out derivative ECC-023 however did not produce any evidence of infectious phage, even when treated to induce the SOS response. The data shows that the BL21 (DE3) derivative ECC-023 does not produce any detectable infectious phage particles and accordingly is a suitable host cell strain for biopharmaceutical manufacturing.

TABLE 1

Production of infectious phase particles from *E. coli*.

| | PFU/ml | |
|---|---|---|
| | Not Induced | SOS Induced |
| BL21(DE3) | 21 | 10,000 |
| ECC-023 | 0 | 0 | medium) at 37° C. until an $OD_{600}$ of 1.0 was reached. Medium compositions for MCJK and MCJKLB are described in Table 2.

TABLE 2

Medium compositions for production of Hexahis-FabZ

| Component | MCJK | MCJKLB |
|---|---|---|
| $K_2HPO_4$ | 56 mM | 56 mM |
| $(NH_4)_2SO_4$ | 38 mM | 38 mM |
| $MgSO_4$ | 5 mM | 5 mM |
| $CaCl_2$ | 1 mM | 1 mM |
| Trace metals* | 1 mL/L | 1 mL/L |
| Glucose | 10 g/L | 10 g/L |
| Yeast extract | none | 5 g/L |
| Bacto-tryptone | none | 10 g/L |

*Trace metals: 161 mM $FeCl_2$, 2.7 mM $Na_2MoO_4$, 1.4 mM $ZnSO_4$, 2.5 mM $MnCl_2$, 3.2 mM $CuSO_4$, 3.4 mM $CoCl_2$, and 3.2 mM $H_3BO_3$ Isopropyl-beta-D-thiogalactopyranoside ("IPTG") was added to a final concentration of 1 mM and the cells were maintained at 37° C. for four hours until harvest. Cells were collected by centrifugation at 16,000×g for 10-min and lysed by gentle agitation in 10 mM Tris, pH 8.0, 1 mM $Na_2EDTA$, 10 μg/mL lysozyme and 25 U/mL Benzonase (Sigma). Cell debris was removed by centrifugation at 16,000×g for 10 minutes and the recombinant protein was purified from the soluble extract with Ni-NTA resin in batch mode according to the manufacturer's recommendations (Qiagen Inc., Valencia, Calif.). Heterologous proteins were analyzed for the presence of the gluconolactone modification by LC/MS analysis.

$MGSSH_4$ His-tag heterologous polypeptide is gluconoylated at a level of 34% of total recombinant protein when the culture is performed in minimal medium (MCJK) as shown in Table 3. When the medium is supplemented or made rich with yeast extract and tryptone, gluconoylated protein is not detectable, also shown in Table 3. Thus, the use of a richer medium can prevent formation of the 6-PGL adduct.

TABLE 3

Effect of minimal vs. rich medium on gluconoylation of a His-tagged protein expressed in *E. coli*

| Vector | N-Terminus | Insert | Modified % | Host | Medium | Comments |
|---|---|---|---|---|---|---|
| pET28FabZSa | $MGSSH_6$ | FabZ | 34% | BL21(DE3) | MCJK | minimal medium |
| pET28FabZSa | $MGSSH_6$ | FabZ | Not detectable | BL21(DE3) | MCJKLB | rich medium |

Example 2

This example shows that culturing cells in a rich medium can prevent formation of a 6-PGL adduct of His-tagged proteins as compared to minimal medium.

*E. coli* BL21 (DE3) transformed with plasmid pET28FabZSa, which encodes the gene for Hexa-his-FabZ, was grown in MCJK (minimal medium) or MCJKLB (rich Example 3

This example demonstrates that an internal lysine residue of a recombinant CXC chemokine (otherwise known as Gro-beta-T) can become gluconoylated when expressed in *E. coli*. The cDNA and amino acid sequences of human Gro-beta-T are provided in International Patent Application, Publication No. WO 92/00327 (Jan. 9, 1992) as well as U.S. Pat. No. 6,042,821 and U.S. Pat. No. 6,413,510, incorporated herein by reference in their entirety.

Heterologous protein accumulation during production of a CXC chemokine (Gro-beta-T) was routinely monitored using a quantitative, high throughput reversed phase assay. This separation was interfaced with a high-performance electrospray time-of-flight ("ESI-TOF") mass spectrometer to provide a means of routinely monitoring formation of product related variants.

When expressed in the E. coli BL21 (DE3) host, two unique product modifications were observed. Deconvolution of the mass spectra characterized the variants as exhibiting mass shifts of +178 Da and +258 Da compared to native product at 7,542 Da.

Product derived from these fermentations was passed through a purification procedure. In-process samples were characterized using a high resolution reversed phase assay that is capable of resolving minor product variants. Liquid chromatography mass spectroscopy ("LCMS") analysis confirmed that the new product variants exhibited mass shifts of +258 Da (ret. time ~14.8 min) and +178 Da (ret. time ~15.2 Da).

Published literature indicated that these +258 Da and +178 Da mass shifts had previously been observed in proteins expressed with hexa His-tags resulting from the addition of 6-PGL or gluconolactone to the N-terminal residue. The CXC chemokine (Gro-beta-T) was not expressed using a hexa His-tags. Furthermore, the molecule does not exhibit any histidine rich regions. To confirm that the species were product related, each variant was isolated and subjected to N-terminal sequencing. Sequencing confirmed proper product sequence and ensured that no hexa His-tag was present.

Variants were subjected to trypsin digestion and peptide mapping. Comparison with peptide maps generated using product standard revealed two new peaks in the tryptic map with the first peak eluting at 45.8 min (m/z 1094) and the second peak eluting at 46.5 min (m/z 1174). The new peptides were isolated and subjected to N-terminal sequencing which indicated that both had the same sequence (NIQSVKVK (SEQ ID NO:4)). The sequence homology and presence of a 80 Da mass difference suggested that the species differed only by the presence of phosphorylation.

LCMS mass spectrometry analysis was performed on the peak with m/z 1174. The MS/MS experiment confirmed the peak has a sequence of NIQSVKVK (SEQ ID NO:4). In addition, the y series fragment ions starting from y3 including y3, y4, y5, and y6 shown mass increase of 258 Da. However, the y2 ion did not show mass increase of 258 Da. This data indicated that the modification was on Lysine (no. 23 in the sequence) with mass increase of 258 Da.

To confirm that the modification observed was due to product gluconoylation, in vitro reactions were developed that employed reactive L-glucono-1,5-lactone or galactonic acid. Previous work had shown that these species were capable of inducing addition of gluconoyl species to the hexa His-tag [Geohegan, et al.].

Purified CXC chemokine (Gro-beta-T) was buffer exchanged into a TRIS buffer at pH 8.0. L-glucono-1,5-lactone or galactonic acid were added to a concentration of 450 mM and samples were incubated at room temperature for twenty minutes. Both lactones induced the same +178 Da modification of the CXC chemokine observed during expression in E. coli.

Example 4

This example illustrates the gluconoylation of internal lysine residues of a recombinant human interleukin (human IL-18) expressed in E. coli.

High resolution reversed phase HPLC coupled with ESI-TOF mass spectrometry was employed to screen an interleukin product for 6-PGL adducts. Analysis of B-strain expressed interleukin yielded a product related species exhibiting a mass difference of +178 Da. Since the protein was expressed without a hexa His-tag, the modification was likely occurring at an internal lysine residue as had been observed with the CXC chemokine (see Example 3).

High resolution reverse phase HPLC analysis of the interleukin molecule enabled identification of multiple product species exhibiting +178 Da mass shifts at RT 21.0, 22.0, 23.0 minutes and an additional minor species exhibiting a +258 Da shift (RT ~27.5 minutes).

In vitro modification of the interleukin was also evaluated with L-glucono-1,5-lactone at pH 8.0, as described in the previous example. This reaction again yielded the same +178 Da modifications observed when the interleukin was expressed in B strain of E. coli.

Example 5

This example shows that culturing cells in rich medium prevents gluconoylation or PGL adduct formation of internal lysine residues of a recombinant protein. Three fed-batch fermentation processes were compared in this study. The difference between the fermentation runs was the batch medium and feed compositions used during the production phase. A rich medium was used in the Process I fermentation, while the second and third batches (Processes II and III) were performed with a minimal medium. Glycerol was used as feed medium in Process I and II, while glucose was used in Process III.

The fermentation process to produce a recombinant interleukin in E. coli was carried out in a fed-batch mode in a 15-liter fermenter. The fermentation was started as a batch process. The inoculum was prepared by aseptically transferring 0.5 mL of a glycerol stock culture into 1000 ml of PYE medium in a 2.8-L flask, as shown in Table 4.

TABLE 4

Seed medium composition for expansion of inoculum into fermenters.

| Item | Batch Medium concentration |
|---|---|
| Yeast Extract | 5 g/L |
| Phytone peptone | 10 g/L |
| Sodium chloride | 10 g/L |
| Dextrose | 10 g/L |
| Kanamycin sulfate | 50 mg/L |

The culture was grown overnight at 27.5° C. on a rotary shaker. The shake flask culture was then transferred into a fermenter containing 5 L of batch medium. The production medium consists of salts, amino acids, and kanamycin sulfate. Additionally, the rich medium is supplemented with high concentrations of yeast extract and phytone peptone, as shown in Table 5.

TABLE 5

Production stage medium composition for comparison of rich vs. minimal medium.

| | Batch Medium Concentration | | |
|---|---|---|---|
| Item | Process I | Process II | Process III |
| Yeast Extract | 48 g/L | 5.8 g/L | 5.8 g/L |
| Phytone peptone | 24 g/L | 1.6 g/L | 1.6 g/L |
| $(NH_4)_2SO_4$ | none | 5 g/L | 5 g/L |
| NaCl | none | 1.3 g/L | 1.3 g/L |
| Dextrose | none | none | 33.5 g/L |
| Glycerol | 26 g/L | 26 g/L | none |
| $K_2HPO_4$ | 15.3 g/L | 6 g/L | 6 g/L |
| $KH_2PO_4$ | 1.7 g/L | 3 g/L | 3 g/L |
| Trace metals* | 1 mL/L | 1 mL/L | 1 mL/L |
| $MgSO_4$ | 5 mM | 5 mM | 5 mM |
| $CaCl_2$ | 1 mM | 1 nM | 1 nM |
| Kanamycin sulfate | 30 mg/L | 30 mg/L | 30 mg/L |

*Trace Metals solution: $FeCl_2 \cdot 6H_2O$, 37.8 g/L; $Na_2MoO_4 \cdot H_2O$, 0.7 g/L; $ZnSO_4 \cdot 7H_2O$, 0.4 g/L; $MnCl_2 \cdot 4H_2O$, 0.5 g/L; $CuSO_4 \cdot 5H_2O$, 0.8 g/L; $CoCl_2 \cdot 6H_2O$, 0.8 g/L; $H_3BO_3$, 0.2 g/L.

The pH of each medium was maintained at approximately 7.3 using ammonium hydroxide. Temperature was controlled at about 27.5° C. Feed medium, glycerol or dextrose was sterilized separately and aseptically connected to a fermenter using silicone rubber tubing.

Supply of feed medium was initiated when the initial batch amount in culture was depleted. A polarographic oxygen electrode monitored dissolved oxygen tension in the fermenter. Carbon feed rate was controlled in a cascade mode to keep constant dissolved oxygen tension above 20%. Aeration was maintained at 10 slpm and pressure at 7.0 psig over pressure. Agitation speed of 800 rpm was used from beginning to the end of the fermentation run. At an $OD_{550}$ of approximately 40 units, 100 mL of 1 mM IPTG was injected into culture to induce recombinant gene expression.

Reverse-phase HPLC analysis of the samples collected 24 hours post IPTG addition indicated reduction in the level of gluconolactone in the product. The absence of 6-PGL adduct in Process I, and its presence in Process II and III, indicates that the use of rich medium, and not glycerol carbon source, was responsible for elimination of the 6-PGL adduct. Table 6 summarizes the results of the analysis.

TABLE 6

Analysis of phosphogluconolactone adduct in three fermentation processes to produce a recombinant interleukin.

| Process No. | phosphogluconolactone adduct on human interluekin (IL-18) |
|---|---|
| Process I | Absent |
| Process II | Present |
| Process III | Present |

Example 6

This example shows that the K-12 strain of *E. coli* has 100-fold higher pgl activity than B strain.

6-Phosphogluconolactonase activity was measured in extracts of two different strains with BL12(DE3) as the parental one, ECC005 and ECO680, and two other strains originated from a K-12 genotype, ECO706 and ATG3995.

To culture the strains, 2-L shake flasks containing 1 L of PYE medium +1% glucose and 50 µg/ml kanamycin were inoculated with 0.4 mL of cell suspension from frozen vials. Incubation was at 30° C., with an agitation of 220 rpm for 6 or 7.5 hours. Samples were taken at the indicated time points to measure the optical density at 550 nm and collect pellets to measure the pgl activity. Details of in vitro assay to measure the pgl activity is presented below.

The pgl activity was assayed fluorimetrically, at 340 nm and 25° C., in cell-free extracts. The cell-free extracts were prepared as previously described (Maitra and Lobo, *Journal of Biological Chemistry* 246: 475-488 (1971)); with essentially the same resuspension buffers, 50 mM-HEPES pH 7.3 containing 5 mM-EDTA and 5 mM-β-mercaptoethanol, but cells were broken by sonication (5 cycles of 20 sec.).

The pgl was assayed using a previously published method (Sinha and Maitra *Journal of General Microbiology*, 1992; 138: 1865-1873) with some modifications. The assay consisted of a pre-incubation of 1 mL-mixture containing 50 µM-glucose-6-phosphate, 0.5 mM-NADP+, and 1 unit of glucose-6-phosphate dehydrogenase in 100 mM-MES buffer, pH 6.5, containing 25 mM-KCl and 10 mM-MgCl2. Once the reaction reached the plateau, it was followed by the addition of 2 units of 6-phosphogluconate dehydrogenase resulting in a slow increase in the absorbance due to the spontaneous hydrolysis of the 6-PGL formed during the pre-incubation step. At the addition of cell-free extracts, any significant increment in the fluorescence is because of the phosphoglunolactonase activity. All pgl activities were estimated in the linear range of the absorbance increase following addition of the cell-free extract.

The enzyme activity was estimated by subtracting the rate of spontaneous hydrolysis of 6-PGL. The enzyme activities were expressed in mmol NADPH per minute and per mg of total protein. Total protein was determined by the Bicinchoninic acid (BCA) Protein Assay (Pierce, Ill., USA).

In the strains based parentally in a K-12 genotype, we have detected upwards of 100-fold more activity than in B strains.

Table 7 summarizes the results of the enzyme assays on the two strain backgrounds.

TABLE 7

Phosphogluconolactonase activity measured in K-12 and B strains of *E. coli*

| Strain | Cultivation Time (h) | Activity (mmol NADH/ min/mg protein) | Sp. Hydrolysis (mmol/min/mg protein) |
|---|---|---|---|
| "K" STRAINS | | | |
| ATCC 10798 | 5.5 | 1.061 | 0.0011 |
| | 6.5 | 2.899 | 0.0012 |
| | 7.5 | 2.584 | 0.0012 |
| K-12 expressing a human interleukin (IL-18) | 7.5 | 3.539 | 0.0011 |
| "B" STRAINS | | | |
| ATCC 47092 | 5.5 | 0.028 | 0.0012 |
| BL21(DE3) expressing a human interleukin (IL-18) | 5.5 | 0.032 | 0.0012 |
| | 6.5 | 0.019 | 0.0011 |
| | 7.5 | 0.032 | 0.0012 |

Example 7

This example shows that expressing a heterologous polypeptide, a CXC chemokine (otherwise known as Gro-beta-T), in *E. coli* BL21 strain results in 6-PGL adduct, whereas expressing the same polypeptide in a K-12 strain prevents gluconoylation of internal lysines.

Ten fermentation runs were carried out using four different strains of *E. coli* constructed to recombinantly express a CXC chemokine. This example demonstrates the effect of host background versus promoter system on the presence of 6-PGL adduct formation of the recombinant protein by using two expression systems with each host cell background. Table 8 describes the strains that were used.

TABLE 8

Host background and promoter systems used to express a CXC chemokine in *E. coli*.

| Strain No. | Host Background | Promoter system |
|---|---|---|
| 1 | BL21 (DE3) | T7 polymerase |
| 2 | K-12 (DE3) | T7 polymerase |
| 3 | BL21 (DE3) | Lambda pL |
| 4 | K-12 | Lambda pL |

Fermentation to produce the CXC chemokine (Gro-beta-T) in *E. coli* was carried out in a fed-batch mode in a 15-liter fermenter. Fermentation was started as a batch process. Inoculum was prepared by aseptically transferring 0.75 mL of a glycerol stock culture into 100 mL of PYE medium in a 500 mL baffled flask. Culture was grown for 7 hours at 32.0° C. on a rotary shaker. Shaken flask culture was then mixed with 1.0 L of PYE medium and transferred into a fermenter containing 8.0 L of batch medium. Production medium consisted of salts and either carbenicillin or kanamycin sulfate depending on the promoter. Media formulations for seed expansion are provided in Table 9, and medium formulation for production of CXC chemokine in *E. coli* are provided in Table 10.

TABLE 9

Medium formulation for seed expansion.

| Component | Concentration |
|---|---|
| Yeast Extract | 5 g/L |
| Phytone peptone | 10 g/L |
| Sodium chloride | 10 g/L |
| Dextrose | 10 g/L |
| Kanamycin sulfate | 50 mg/L |

TABLE 10

Medium formulation for production of CXC chemokine in *E. coli*

| Component | Concentration |
|---|---|
| Ammonium Sulfate | 5 g/L |
| Potassium phosphate, Dibasic | 6 g/L |
| Potassium phosphate, Monobasic | 3 g/L |
| Sodium chloride | 1.3 g/L |
| Dextrose | 18 g/L |
| Magnesium sulfate | 4.8 g/L |
| Biotin | 1 mg/L |
| Trace Metals* | 10 mL/L |
| Kanamycin sulfate | 50 mg/L |
| -or- | |
| Carbenicillin | 25 mg/L |

*Trace Metals solution: $FeCl_2 \cdot 6H_2O$, 3.78 g/L; $Na_2MoO_4 \cdot H_2O$, 0.7 g/L; $ZnSO_4 \cdot 7H_2O$, 0.4 g/L; $MnCl_2 \cdot 4H_2O$, 0.5 g/L; $CuSO_4 \cdot 5H_2O$, 0.8 g/L; $CoCl_2 \cdot 6H_2O$, 0.8 g/L; $H_3BO_3$, 0.2 g/L.

pH of each medium was maintained at about 7.0 using ammonium hydroxide. Temperature was controlled at about 32.0° C. and increased to about 37.5° C. at induction. Feed medium and dextrose were sterilized separately and aseptically connected to a fermenter using silicone rubber tubing.

Supply of feed medium was initiated when the initial batch amount in the culture was depleted. A polarographic oxygen electrode monitored dissolved oxygen tension in the fermenter. Carbon feed rate was controlled in a cascade mode to keep constant dissolved oxygen tension above about 25%. Aeration was maintained at about 10 slpm and the pressure at about 7.0 psig over pressure. Agitation speed of about 400 rpm was used at the beginning and increased as required to maintain about 25% dissolved oxygen tension. At an $OD_{550}$ of approximately 14 units, 100 mL of 1.0 mM IPTG was injected into the culture, or the temperature was increased to 37.5° C. to induce recombinant gene expression.

None of the fermentation runs using a K-12 host background had detectable 6-PGL adduct formation on recombinantly expressed polypeptide, whereas runs using B strain in concert with T7 promoter all exhibited the presence of detectable 6-PGL adduct formation on recombinantly expressed polypeptide. The three runs using B strain and the pL promoter did not have detectable adduct formation. These data demonstrate that expressing a recombinant protein in a host strain having pgl activity, e.g. K-12, may prevent 6-PGL adduct formation in recombinant proteins that are susceptible to this modification, see Example 3. The presence of 6-PGL adduct formation in CXC chemokine expressed in *E. coli* B and K-12 strains is presented for each fermentation in Table 11.

TABLE 11

Presence of 6-PGL adduct on CXC chemokine expressed by T7 or pL promoter in *E. coli* B and K-12 strains.

| Strain genotype | Promoter | Run No. | Gluconolactone adduct 5 hr post induction [% of product peak] |
|---|---|---|---|
| B | T7 | 1 | 21.7 |
| | | 2 | 5.8 |
| | | 3 | 4.2 |
| | | Average | 10.6 |
| K-12 | T7 | 1 | 0 |
| | | 2 | 0 |
| | | Average | 0 |
| B | pL | 1 | 0 |
| | | 2 | 0 |
| | | 3 | 0 |
| | | Average | 0 |
| K12 | pL | 1 | 0 |
| | | 2 | 0 |
| | | Average | 0 |

Example 8

This example shows that expressing a heterologous polypeptide, human interleukin (human IL-18), in *E. coli* BL21 strain results in 6-PGL adduct formation, whereas expressing the same polypeptide in a K-12 strain will prevent 6-phosphogluconoylation of internal lysines.

*E. coli* BL21 (DE3) and K-12 strains were constructed to express a human interleukin (IL-18). Cultures were grown in minimal medium as described in Example. Monitoring for product modification with 6-PGL was conducted at various time points throughout the culture, using methods described in Example.

Results are expressed as peak area ratios of unmodified product to modified product. Higher numbers indicate a lesser proportion of gluconoylated product. It is evident that the extent of gluconoylation in BL21 (DE3) strain is significantly greater than in K-12 strain. Phosphogluconoylation of a human interleukin (IL-18) expressed in B and K-12 strains of E. coli is summarized in Table 12.

TABLE 12

Phosphogluconoylation of a human interleukin expressed in B and K-12 strains of E. coli

| E. coli strain | Time post induction (h) | Area ratio of unmodified product to modified product |
|---|---|---|
| K-12 | 16 | 58.4 |
|  | 18 | 44.5 |
|  | 20 | N/d |
|  | 22 | 29.3 |
|  | 24 | 30.0 |
| BL21(DE3) | 22 | 8.3 |
|  | 24 | 7.7 |

N/d = modified product not detectable

Example 9

This example illustrates that overexpression of heterologous pgl in E. coli host cells leads to increased metabolic conversion of 6-PGL to its product 6-phosphogluconate thereby reducing the pool of 6-PGL available for adduct formation. A P. aeruginosa pgl gene was cloned and engineered into a plasmid based inducible expression vector system that is compatible with colE1 origin of replication based plasmids, such that two different plasmids may be maintained in the same host cell. The inducible expression level of P. aeruginosa pgl can be regulated at will, in a fashion independent of endogenous E. coli metabolic pathways and independent of the inducible expression of the recombinant protein of interest. Accordingly, recombinant pgl expression can be regulated such that the pool of 6-PGL was diminished below the level required for adduct formation, but not to the extent that host cell resources were substantially affected. Therefore, the level of the desired recombinant protein can be separately regulated to give very high expression levels.

Cloning of P. aeruginosa pgl.

P. aeruginosa pgl was cloned as follows. P. aeruginosa was obtained from the American Type Culture Collection (American Type Culture Collection, 12301 Parklawn Drive, Rockville Md. 20852-1776): Pseudomonas aeruginosa, strain ATCC 27853. 5' and 3' PCR amplification primers were designed and synthesized to direct the PCR amplification of the entire pgl gene, including the region just upstream of the initiation codon ATG. The sequence of the sense and antisense amplification primers are:

```
                                            (SEQ ID NO: 4)
5' GGCCTCGAGCTCGGTGGCCCTGGTGGCCC 3'
and
                                            (SEQ ID NO: 5)
5' GCCCTCGAGTCCGCCACTCAGGGGTACCAAT 3'
``` respectively. Bolded sequences indicate XhoI sites introduced into the gene to enable subsequent cloning steps.

It was additionally found that the P. aeruginosa gene is very GC-rich and will not PCR amplify under normal amplification conditions. It was found that PCR amplification requires the use of PCR amplification conditions that are optimized for GC-rich templates, specifically Advantage-GC cDNA Polymerase Mix (cat. 8419-1; BD Biosciences Clontech:Palo Alto, Calif.; USA). The corresponding pgl DNA sequence (SEQ ID NO:7) encoding the polypeptide SEQ ID NO:8 was PCR amplified from whole P. aeruginosa cells after 25 cycles of 94° C. for 30 seconds followed by 68° C. for 1.5 minutes. The amplification was then completed by a single incubation at 68° C. for 3 minutes. The PCR product was isolated by agarose gel electrophoresis and column chromatography over a QIAquick Gel Extraction Kit (cat. 28704, Qiagen: Valencia, Calif.; USA). The amplified, gel purified pgl DNA was eluted in water and immediately cloned into the cloning vector pCR2.1 using a TOPO TA Cloning® kit (cat. K4550-40, Invitrogen: Carlsbad, Calif.; USA) and transformed into One Shots TOP10 Chemically Competent E. coli (cat. C4040-06, Invitrogen: Carlsbad, Calif.; USA). Resulting amp$^r$ colonies were screened for inserts by EcoRI digestion and electrophoresis of the products. Sequence verified inserts were released from the cloning vector by XhoI digestion and purified using the QIAquick Gel Extraction Kit. pECO-1 expression vector DNA (BioCat 73552, GlaxoSmithKline: King of Prussia, Pa.; USA) was cut with SalI and treated with Calf Intestinal Alkaline Phosphatase (CIP) (cat M0290S, New England Biolabs:Beverly, Mass.; USA), and then purified using the QIAquick Gel Extraction Kit. The XhoI digested inserts and the SalI treated pECO-1 were ligated using T4 DNA ligase essentially as described by the manufacturer (cat. M0202S; New England Biolabs: Beverly, Mass.; USA). Two microliters (2 µl) of the ligation reaction was transformed into One Shot® TOP10 chemically Competent E. coli cells as described by the manufacturer (cat. C4040-06; Invitrogen: Carlsbad, Calif.; USA). Colonies were screened for the presence pgl inserts in the correct orientation by PCR. Clone pECO-1pglcl2-13 was selected for further study as set forth below.

The resulting construct is based on the pACYC184 plasmid backbone, and comprises the following genetic functional elements: (1) p15A ori, which allows plasmid episomal maintenance in the same host cell as heterologous plasmids with the colE1-type ori element; (2) chloramphenical$^r$ selectable marker; (3) a tetracycline inducible promoter upstream of a multiple cloning site; (4) the full length P. aeruginosa pgl gene.

The final construct, pECO-1 pglcl2-13, was transformed as described above into BL21 (DE3) cells expressing a human interleukin for further study. The DNA sequence of pECO-1pglcl2-13 sequence is presented as SEQ ID NO:9 and the restriction map of pECO-1 pglcl2-13 is presented in FIG. 1.

Cultures were performed as described in Example 3. Analysis for 6-PGL adduct was performed as described in Example 4. Phosphogluconolactonase activity was measured as described in Example 6. Additional strains expressing the human interleukin (IL-18) that were examined in the study include BL21 (DE3) without pECO-1 pglcl2-13 and K-12. The strains with the pgl plasmid were examined with and without the addition of anhydrotetracycline at 20 ng/mL. A summary of the presence of absence of 6-PGL adduct formation in cells expressing pgl is summarized in Table 13 as shown below.

TABLE 13

Impact of pgl expression on phosphogluconoylation of a human interleukin

| Strain | Maximum pgl activity IU/min/g DCW | 6-PGL adduct formation on human interleukin (IL-18) |
|---|---|---|
| BL21 (DE3) | 0.002 | Present |
| BL21 (DE3) pECO-1pglcl2-13, no tet | 0.56 ± 0.13 | Absent |

TABLE 13-continued

Impact of pgl expression on phosphogluconoylation of a human interleukin

| Strain | Maximum pgl activity IU/min/g DCW | 6-PGL adduct formation on human interleukin (IL-18) |
|---|---|---|
| BL21 (DE3) pECO-1pglcl2-13, tet induced | 0.64 ± 0.11 | Absent |
| K-12 | 0.96 ± 0.14 | Absent |

DCW = dry cell weight

This example has demonstrated that co-expression of Pseudomonas phosphogluconolactonase with the human interleukin (IL-18) successfully prevents formation of the 6-PGL adduct in the B strain of E. coli.

Example 10

Human interleukin-18 (IL-18) is an immunomodulatory cytokine that is being developed as an anti-cancer agent for the treatment of renal cell carcinoma and malignant melanoma. Descriptions of human and murine IL-18 are presented in the following U.S. patents: U.S. Pat. No. 6,582,689, U.S. Pat. No. 5,914,253, U.S. Pat. No. 5,879,942, U.S. Pat. No. 5,912,324, U.S. Pat. No. 5,914,253, U.S. Pat. No. 6,060,283, U.S. Pat. No. 6,087,116, and U.S. Pat. No. 6,214,584, which are incorporated herein by reference in their entirety. IL-18 is believed to stimulate the immune system, promote Fas-induced tumor cell death and cell mediated immunity. The polypeptide sequence of IL-18 (SEQ ID NO:10) may be produced in E. coli BL21(DE3). It may be expressed from the polynucleotide sequence for pro-IL18 (SEQ ID NO:11), which is further processed to mature IL-18 by a processing enzyme, Caspase 5, co-expressed in the same cell.

6-Phosphogluconolactonase from Gram-negative bacterium, Pseudomonas aeruginosa, was cloned into a BL21 (DE3) strain. Production of IL-18 in this strain produces IL-18 with no detectable adduct formation resulting in a direct increase in the yield of the desired product. Furthermore, the correction of the pgl deficiency has also resulted in >10% increase in specific productivity. Thus, the combined effect of product quality and specific productivity improvements by the use of this modified production strain has translated into a >25% increase in titer yield at the fermentation stage. It is anticipated that the elimination of adduct formation will have a direct, positive impact on the purification process and further increase the overall process yield.

Example 11

Gluconoylation of IL-18 was monitored by HPLC analyses on IL-18 produced in BL21 (DE3) cells with and without co-expression of pgl. Adduct formation was detected as a shoulder peak eluting approximately two minutes after purified IL-18. When IL-18 was expressed in and purified from E. coli strain BL21DE3 (pgl minus), the main peak area (i.e., area of the peak for IL-18 having no detectable gluconoyl adduct formation) for IL-18 was approximately 56%. While expression and purification of IL-18 is BL21 (DE3) (pgl plus) cells produced a main peak area of about 88% and showed no adduct formation based on the High Resolution HPLC assay."

Example 12

Two vectors were created comprising polynucleotides that encode pro-IL-18 (SEQ ID NO: 11), Caspase 5 (SEQ ID NO:12). Both were pET vectors wherein polypeptide production was induced using a T7 promoter. One vector also comprised a polynucleotide encoding pgl from P. aeruginosa (SEQ ID NO:7) that was induced by the same promoter as pro-IL-18. The entire sequence of the pET vector comprising pro-IL-18 and Caspase 5 is presented in SEQ ID NO:13. A restriction map of this vector is presented in FIG. 2. The entire sequence of the pET vector comprising pro-IL-18, Caspase 5 and pgl is presented in SEQ ID NO:14. A restriction map of this vector is presented in 3. When IL-18 was expressed in E. coli BL21 (DE3) cells using these vectors, the amount of recoverable IL-18 was greatly improved when the polypeptide was co-expressed with pgl compared with the expression of IL-18 without pgl. The amount of recovered IL-18 obtained from each expression vector in E. coli BL21 (DE3) cells is presented in Table 14.

TABLE 14

IL-18 Maximum Titer Produced in "B" Strain E. coli with and without Co-expression of pgl

| Strain* | pgl gene | Maximum Titer (g/L) |
|---|---|---|
| RBB057 | No | 4.32 (+/−0.4) |
| RBB059 | Yes | 6.78 (+/−0.1) |

*Both strains are E. coli B strain

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

The invention claimed is:

1. A method for reducing gluconoylation of a heterologous polypeptide expressed in *E. coli*, wherein said heterologous polypeptide is human IL-18, said method comprising growing said *E. coli* in rich culture medium, wherein the amount of gluconoylation on said human IL-18 is reduced as compared to *E. coli* grown in minimal medium.

2. The method of claim 1, wherein the *E. coli* does not demonstrate significant 6-phosphogluconolactonase activity when grown in minimal medium.

3. The method of claim 1, wherein the *E. coli* is B strain.

4. The method of claim 1, wherein the rich culture medium comprises a complex nitrogen source.

5. The method of claim 4, wherein the rich culture medium is capable of maintaining cell growth at ratio of 1:1 for concentration of complex nitrogen source to cell density.

6. The method of claim 4, wherein the complex nitrogen source comprises tryptone.

7. The method of claim 4, wherein the complex nitrogen source comprises peptone.

8. The method of claim 4, wherein the complex nitrogen source comprises yeast extract.

9. The method of claim 1, wherein the culture medium is Superbroth.

10. The method of claim 9, wherein the Superbroth medium is doubly concentrated.

* * * * *